(12) United States Patent
Leclerc et al.

(10) Patent No.: US 7,083,928 B2
(45) Date of Patent: Aug. 1, 2006

(54) DETECTION OF NEGATIVELY CHARGED POLYMERS USING WATER-SOLUBLE, CATIONIC, POLYTHIOPHENE DERIVATIVES

(75) Inventors: Mario Leclerc, Québec (CA); Hoang Anh Ho, Sainte-Foy (CA); Maurice Boissinot, St-Augustin-de-Desmaures (CA)

(73) Assignees: Infectio Diagnostic (I.D.I.), Inc., Quebec (CA); Universite' Laval, Quebec (CA)

( * ) Notice: Subject to any disclaimer, the term of this patent is extended or adjusted under 35 U.S.C. 154(b) by 0 days.

(21) Appl. No.: 10/474,230

(22) PCT Filed: Apr. 5, 2002

(86) PCT No.: PCT/CA02/00485

§ 371 (c)(1),
(2), (4) Date: Apr. 5, 2004

(87) PCT Pub. No.: WO02/081735

PCT Pub. Date: Oct. 17, 2002

(65) Prior Publication Data

US 2004/0171001 A1 Sep. 2, 2004

Related U.S. Application Data

(60) Provisional application No. 60/288,442, filed on May 4, 2001, provisional application No. 60/284,184, filed on Apr. 18, 2001, provisional application No. 60/281,371, filed on Apr. 5, 2001.

(51) Int. Cl.
  *C12Q 1/68* (2006.01)
  *C07D 333/34* (2006.01)
  *C07D 233/02* (2006.01)
  *C08F 4/06* (2006.01)
  *C07H 21/02* (2006.01)

(52) U.S. Cl. .............................. 435/6; 549/65; 526/90; 548/315.1; 536/23.1; 536/24.3; 536/24.33

(58) Field of Classification Search .................... 435/6; 549/65; 526/90; 548/315.1
See application file for complete search history.

(56) References Cited

FOREIGN PATENT DOCUMENTS

| DE | GB 1278 348 A | 6/1972 |
|---|---|---|
| WO | WO 98/03499 | 1/1998 |
| WO | WO 99/26729 | 6/1999 |

OTHER PUBLICATIONS

Asanov et al., "Effect of surface electrostatics on adsorption behavior and biospecific interactions of dna oligonucleotides," *SPIE*, 5803: 170-177, 1999.

Balanda et al., "Watersoluble and blue luminescent cationic polyelectrolytes based on lpoly (p-phenylene)," *Macromolecules*, 32:3970-3978, 1999.

(Continued)

*Primary Examiner*—Jezia Riley
(74) *Attorney, Agent, or Firm*—Knobbe, Martens, Olson & Bear LLP

(57) ABSTRACT

Novel methods allowing for the simple optical and electrochemical detection of double-stranded oligonucleotides are disclosed. The methods are rapid, selective and versatile. Advantageously, they do not require any chemical reaction on the probes or on the analytes since they are based on different electrostatic interactions between cationic poly (3-alkoxy-4-methylthiophene) derivatives and single-stranded or double-stranded (hibridized) oligonucleotides.

19 Claims, 21 Drawing Sheets

OTHER PUBLICATIONS

Bauerle and Emge, "Specific recognition of nucleobase-functionalized polythiophenes," *Adv. Mater.*, 3:324-330, 1998.

Bonhote et al., "Hydrophobic, highly conductive ambient-temperature molten salts," *Inorg. Chem.*, 35:1168-1178, 1996.

Bronich et al.., "Recognition of dna topology in reactions between plasmid dna and cationic copolymers," *J American Chem. Soc.*, 122:8339-8343, 2000.

Chayer et al., "Highly conducting water-soluble polythiophene derivatives," *Chem. Mater.*, 9:2902-2905, 1997.

Chen et al., "Highly sensitive biological and chemical sensors based on reversible fluorescence quenching in a conjugated polymer," *PNAS*, 96:122287-12292, 1999.

Chrisey et al., "Covalent attachment of synthetic dna to self-assembled monolayer films," *Nucleic Acids Research*, 24:3031-3039, 1996.

Ewbank et al., "Amine functionalized polythiophenes:synthesis and formation of chiral, ordered structures on dna substrates," *Tetrahedron Letters*, 42:155-157, 2001.

Faid and Leclerc, "Responsive supramolecular polythiophene assemblies," *J. Am. Chem. Soc.*, 120:5274-5278, 1998.

Flink et al., "Self-assembled monolayers on gold for applications in chemical sensing," *Reinhoudt in Sensors Update*, Ed. H. Baltes, W. Gopel, J. Hesse, 8:3-19, 2001.

Fodor et al., "Light-directed, spatially addressable parallel chemical synthesis," *Science*, 251:767-773, 1991.

Garnier et al., "Toward intelligent polymers: dna sensors based on oligonucleotide-functionalized polypyrroles," *Synthetic Metals*, 100:89-94, 1999.

Kassmi et al., "Aromatic nucleophilic substitution on thiophene rings," *J. of Molecular Catalysis*, 72:299-305, 1992.

Korri-Youssoufi et al., "Toward bioelectronics: specific dna recognition based on an oligonucleotide-functionalized polypyrrole," *J. Am. Chem. Soc.*, 119:7388-7389, 1997.

Kumar et al., "Silanized nucleic acids: a general platform for dna immobilization,"*Nucleic Acids Research*, 28:I-vi, 2000.

Leclerc, "Optical and electrochemical transducers based on functionalized conjugated polymers," *Adv. Mater.*, 11:1401-1409; 1999.

Lenigk et al., "Surface characterization of a silicon-chip-based dna microarray," *Langmuir*, 17:2497-2501, 2001.

Livache et al., "Preparation of a dna matric via an electro-chemically directed copolymerization of pyrrole and oligonucleotides bearing a pyrrole group," *Nucleic Acids ResearchI*,22:2915-2921, 1994.

Lucas et al., "Expedient synthesis of symmetric aryl ketones and of ambient-temperature molten salts of imidazole," *Synthesis*, 9:1253-1258, 2000.

Lukkari et al., "Polyelectrolyte multilayers prepared from water-soluble poly(alkoxythiophene) derivatives," *J. Am. Chem. Soc.*, 123:6083-6091, 2001.

Lvov et al., "Assembly of thin films by means of successive deposition of alternate layers of dna and poly(allylamine)," *Macromolecules*, 26:5396-5399, 1993.

Lvov et al., "Direct electrochemistry of myoglobin and cytochrome P450 cam in alternate layer-by-layer films with dna and other polyions," *J. Am. Chem. Soc.*, 120:4073-4080, 1998.

McQuade et al., "Conjugated polymer-based chemical sensors," *Chem. Rev.*, 100:2537-2574, 2000.

Mikkelsen, "Electrochemical biosensors for DNA sequence detection," *Electroanalysis*, 8:15-19, 1996.

Peterlinz et al., "Observation of hyridization and dehybridization of thiol-tethered dna using two-color surface plasmon resonance spectroscopy," *J. Am. Chem. Soc.*, 119:3401-3402, 1997.

Peterson et al., "The effect of surface probe density on dna hybridization," *Nucleic Acids Research*, 29:5163-5168, 2001.

Rogers et al., "Immobilization of oligonucleotides onto a glass support via disulfide bonds: a method for preparation of dna microarrays," *Analytical Biochemistry*, 266:23-30, 1999.

Steel et al., Immobilization of nucleic acids at solid surfaces: effect of oligonucleotids length on layer assembly, *Biophysical Journal*, 79:975-981, 2000.

Taton et al., "Scanometric dna array detection with nanoparticle probes," *Science*, 289:1757-1760, 2000.

Tyagi and Kramer, "Molecular beacons: probes that fluoresce upon hybridization," *Nature Biotechnology*, 14:303-308, 1996.

Zammatteo et al., "Comparison between different strategies of covalent attachment of dna to glass surfaces to build dna microarrays," *Analytical Biochemistry*, 280:143-150, 2000.

International Search Report of International Application No. PCT/CA/02/00485 mailed Jan. 14, 2003.

DETECTION OF NEGATIVELY CHARGED POLYMERS USING WATER-SOLUBLE, CATIONIC, POLYTHIOPHENE DERIVATIVES

This application is a U.S. National Phase Application under 35 U.S.C. § 371 of International Application No. PCT/CA02/00485 filed 5 Apr. 2002, which claims the benefit of U.S. Provisional Application Nos. 60/288,442, filed 4 May 2001, 60/284,184, filed 18 Apr. 2001, and 60/281,371, filed 5 Apr. 2001. The entire text of these applications are specifically incorporated into this specification by reference.

FIELD OF THE INVENTION

The present invention relates to simple and reliable methods for negatively charged polymer detection, namely for sequence-selective nucleic acid detection. More specifically, the present invention relates to sequence-selective nucleic acid detection methods, which are essential for the rapid diagnosis of infections and a variety of diseases.

BACKGROUND OF THE INVENTION

Complexes of polythiophene derivatives bearing sulfonic acid moieties and one or several adequately designed amine-containing molecules (electrostatic interactions) have been shown to be responsive to external stimuli (PCT/CA98/01082). More specifically, they were shown to undergo striking conformational changes when exposed to heat, light or various chemical and biochemical moieties giving rise to thermochromism, photochromism, ionochromism or even biochromism. These sulfonic acid-bearing polythiophene derivatives are not positively charged and thus do not have any particular affinity for negatively charged polymers.

The search for methods for sequence-selective nucleic acid detection has evolved into an important research field and has subsequently drawn the attention of researchers from various disciplines such as chemistry, physics, biochemistry, etc. As a result, some interesting DNA hybridization sensors have recently been proposed.[1,5]

However, most of these newly developed approaches perform detection by attaching a fluorescent or electroactive tag to the analyte.

Assays that do not require nucleic acid functionalization prior to detection are of greater fidelity and several research groups have reported the utilization of conjugated field-responsive polymers (polypyrroles, polythiophenes, etc.) as electrochemical or optical transducers.[6,7,23,24] Indeed, the ability of some oligonucleotide-functionalized conjugated polymers to transduce hybridization events into an electrical or optical signal, without utilizing any labeling of the analyte, has been demonstrated.[8-10] The detection mechanism is based on a modification of the electrical and/or optical properties through the capture of the complementary oligonucleotides.

There thus remains a need for simpler, more sensitive and more reliable methods for the rapid and specific identification of nucleic acids. These nucleic acids could be used for the diagnosis of infections and disease. Ideally, an assay that does not require nucleic acid functionalization (chemical manipulation of nucleic acids) prior to detection nor complex reaction mixtures would have the following characteristics: it would be simpler to use than the assays currently available and it would have a high degree of fidelity. Such an assay would be highly beneficial and therefore very desirable.

The present invention seeks to meet these and other needs.

SUMMARY OF THE INVENTION

In general terms, the present invention relates to novel cationic, water-soluble polythiophene derivatives, which can readily transduce oligonucleotide hybridization into a clearly interpretable optical (colorimetric, fluorescent or luminescent) or electrical signal. These polymers can discriminate between specific and non-specific hybridization of nucleic acids differing by only a single nucleotide.

Specifically, the present invention relates to the synthesis and use of cationic water-soluble polymers composed of thiophene monomers having the following general formula:

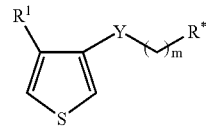

wherein "m" is an integer ranging from 2 to 3; $R^*$ is a quaternary ammonium; Y is an oxygen atom or a methylene; and $R^1$ is a methyl group or a hydrogen atom.

The present invention further comprises a method for detecting the presence of negatively charged polymers, comprising the steps of:
  a) contacting a complementary target to the negatively-charged polymer with a thiophene polymer to form a duplex;
  b) contacting the duplex with the negatively charged polymer; and
  c) detecting a change in electronic charge, fluorescence or color as an indication of the presence of the negatively charged polymer.

The negatively charged polymers for the method as described above, may be selected from the group consisting of: acidic proteins, glycosaminoglycans, hyaluronans, heparin, chromatographic substrates, culture substrates and nucleic acids.

The present invention additionally comprises a method for discriminating a first nucleic acid from a second nucleic acid, the second nucleic acid differing from the first nucleic acid by at least one nucleotide, comprising the steps of:
  a) contacting a complementary target to the first nucleic acid with a thiophene polymer to form a duplex;
  b) contacting the duplex with the first nucleic acid, resulting in specific hybridization;
  c) contacting the duplex with the second nucleic acid, resulting in non-specific hybridization; and
  d) detecting a change in electronic charge, fluorescence or color Finally, the present invention contemplates a number of specific applications, such as the use of a positively charged polymer comprising a repeating thiophene moiety for detecting the presence of negatively charged polymers, and for purifying negatively charged polymers.

Further scope and applicability will become apparent from the detailed description given hereinafter. It should be understood however, that this detailed description, while indicating preferred embodiments of the invention, is given by way of illustration only, since various changes and modifications within the spirit and scope of the invention will become apparent to those skilled in the art.

DETAILED DESCRIPTION OF THE INVENTION

Figure 1:
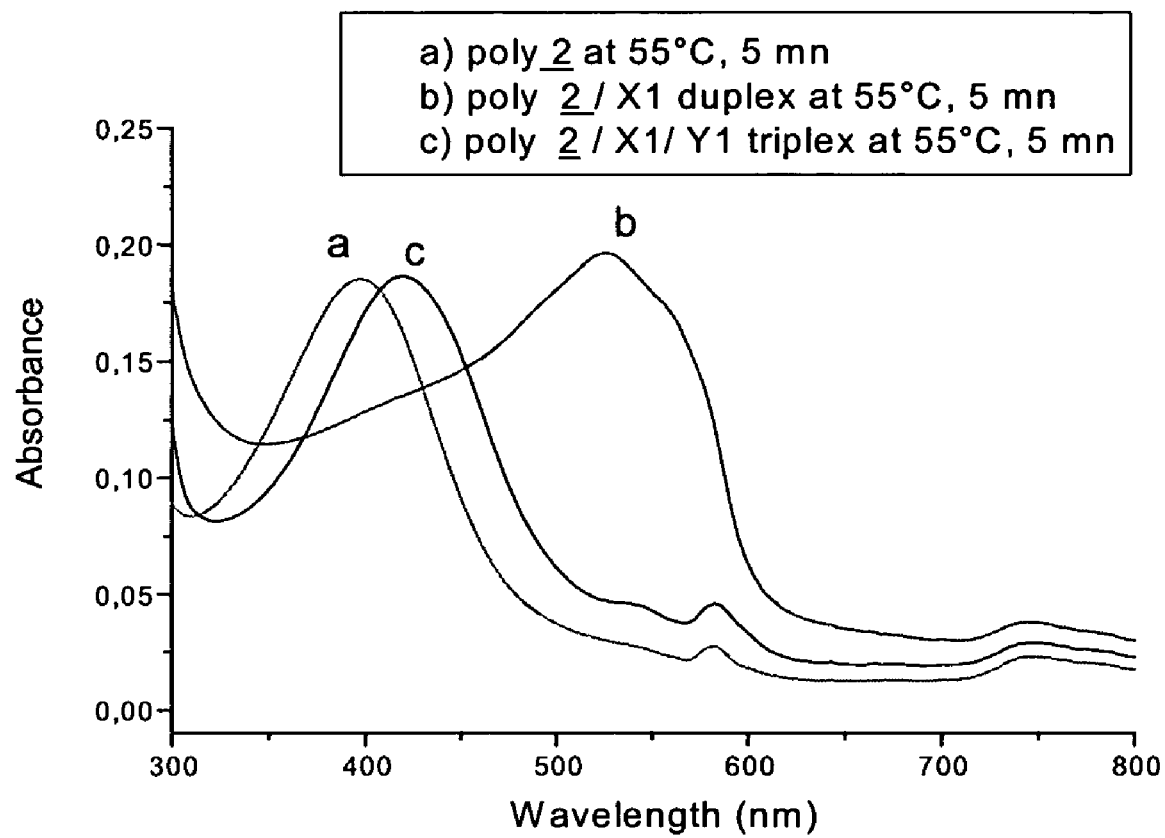
FIG. 1 shows the UV-visible absorption spectrum of a $2.4 \times 10^{-5}$ M (on a monomeric unit basis) solution of: a) polymer 2; b) polymer 2/X1 duplex; c) polymer 2/X1/Y1 triplex, at 55° C. in 0.1M NaCl/H$_2$O using an optical path length of 1 cm.

Other objects and attendant features of the present invention will become readily appreciated, as the same becomes better understood by reference to the following detailed description of the invention described for the purpose of illustration.

In a broad sense, the invention provides novel cationic, water soluble polythiophene derivatives that produce a clearly interpretable optical (colorimetric, fluorescent or luminescent) or electrical signal, when bound to negatively charged polymers.

The present invention provides for polymers capable of discriminating between specific and non-specific hybridization of nucleic acids differing by only a single nucleotide.

The present invention provides improved research tools. More specifically, a means for detecting nucleic acids from eucaryotic organisms as well as prokaryotic organisms such as Bacteria and Archaea.

The present invention also provides for the development of new nucleic acid detection technology, and more specifically, new detection devices based on the use of the polythiophene derivatives of the present invention.

The present invention further provides for improved clinical diagnostics, that is, the detection of infectious agents, the diagnosis of genetic diseases and tools useful for use in the pharmacogenomics field.

The present invention further provides for improved medico-legal (forensic) diagnostics, more specifically the filiation of people and animals, "forensic" tools and other genetic testing tools.

The present invention also provides for improved plant identification.

The present invention also provides for environmental and industrial screening, more specifically for the detection of genetically modified organisms, the detection of pathogenic agents, alimentary tracability, the identification of organisms of industrial interest (e.q. alimentary, pharmaceutical or chemical fermentation and soil decontamination).

The present invention also provides for polythiophenes having an affinity for negatively charged polymers such as nucleic acids and glycosaminoglycans of natural or synthetic origin, allowing for the purification of these polymers. For example, when a polythiophene is coupled to a solid support, nucleic acids can be purified by affinity and/or ion exchange chromatography.

The present invention also provides for polythiophenes that are thermostable and autoclavable, allowing for a wide range of applications.

The present invention further provides methods and tools by which negatively charged polymers such as acidic proteins (kinesins), glycosaminoglycans (hyaluronans, heparin) and any natural or synthetic negative polymers can be detected or blocked by binding with the polythiophenes.

Advantageously, this novel approach is rapid, specific, sensitive, and highly versatile, yet simple. It is based on the different electrostatic interactions and conformational structural changes between single-stranded or double-stranded negatively-charged oligonucleotides or nucleic acid fragments, and cationic electroactive and photoactive poly(3-alkoxy-4-methylthiophene) derivatives. It allows a single reagent assay procedure for genomic analysis and molecular diagnostics. Furthermore, the above mentioned detection methods can also be used for solutions of nucleic acids, nucleic acids separated by gel electrophoreses, nucleic acids fixed onto solid supports such as glass slides or plates, silicon chips or other polymers.

Synthesis

Set forth below are preferred synthesis schemes for the preparation of the water-soluble, cationic, electroactive and photoactive poly(3-alkoxy-4-methylthiophene)s.

The synthesis of monomer 1 is carried out in a two-step procedure, starting from 3-bromo-4-methylthiophene (Aldrich Co.) (see Scheme 1). The first step is a nucleoplilic substitution reaction onto the thiophene ring catalyzed by CuI, as reported by El Kassmi et al.[11] The second step involves a quaternization reaction between the tertiary amine and 1-bromoethane in acetonitrile.[12]

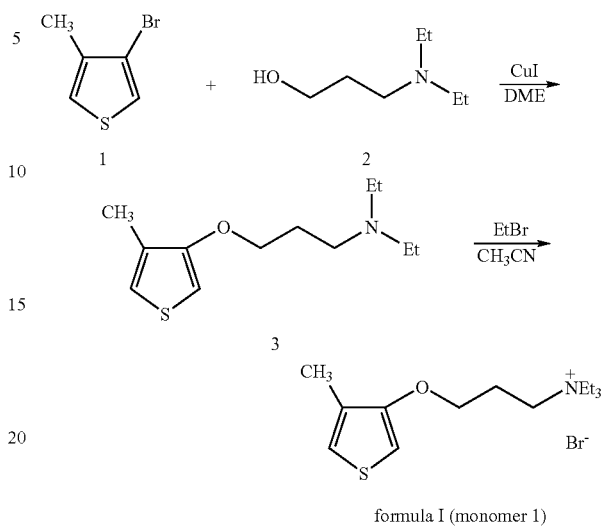

formula I (monomer 1)

Similarly, monomer 2 is prepared from 3-(2-bromoethoxy)-4-methylthiophene (compound 4) and 1-methylimidazole (Aldrich Co.) (see Scheme 2). Compound 4 is prepared according to the procedure developed by Leclerc et al.[13] The quaternization reaction between 1-methylimidazole and compound 4, provides the desired monomer imidazolium salt 2.[14]

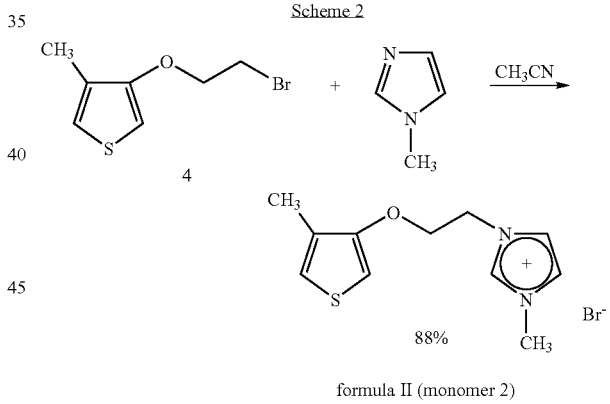

formula II (monomer 2)

Similarly, the synthesis of monomer 3 involves the conversion of 3-thiopheneethanol (compound 5) into its corresponding mesylate protected derivative (compound 6). The quaternization reaction between 1-methylimidazole and compound 6, provides the desired monomer imidazolium salt 3.

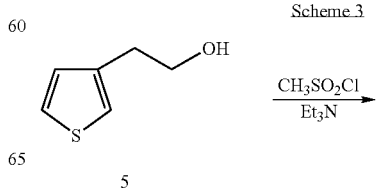

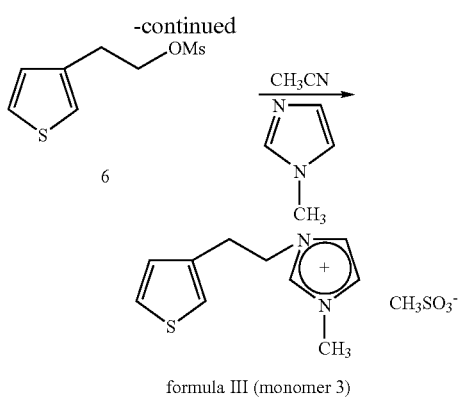

formula III (monomer 3)

The synthesis of monomer imidazolium salt 4 involves a quaternization reaction of compound 4 with 1,2-dimethylimidazole.

Scheme 4

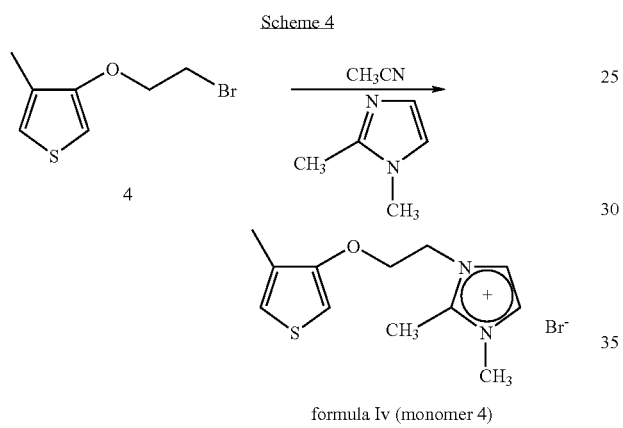

formula Iv (monomer 4)

A more general procedure reflecting the preparation of cationic thiophene monomers is depicted in scheme 5, wherein "m" is an integer equal to 2 or 3; "Y" is an oxygen atom or a methylene group; and $R^1$ is a hydrogen atom or a methyl group.

Scheme 5

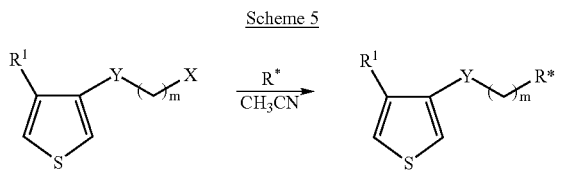

When R* is $Et_3N$, Y is an oxygen atom and $R^1$ is a methyl group, then "m" is equal to 3. When R* is 1-methylimidazole, Y is an oxygen atom and $R^1$ is a methyl group, then "m" is equal to 2. When R* is 1-methylimidazole, Y is a methylene group and $R^1$ is a hydrogen atom, then "m" is equal to 2. When R* is 1,2-dimethylimidazole, Y is an oxygen atom and $R^1$ is a methyl group, then "m" is equal to 2.

The inherent chemical and physical properties of imidazole provide for a wide electrochemical window, favorable for electrochemical detection.[15]

All polymers, more specifically the cationic, water soluble, electroactive polymers 1, 2, 3 and 4 (Scheme 6), were synthesized by oxidative chemical polymerization of the corresponding monomers using $FeCl_3$ or $K_2S_2O_8$ as the oxidizing agent in chloroform. This method of polymerization yields well-defined regio-regular 3-alkoxy-4-methylthiophene polymers (1, 2 and 4) as well as a non-regioregular 3-alkylthiophene polymer (3), having an average molecular weight of about 5 kDa and a polydispersity index of ca. 3.[16] Note that "n" can vary from 3 to about 100. The resulting polymers (using $FeCl_3$ as the oxidizing agent) contain a mixture of anions such as $FeCl_4^-$, $Cl^-$ and $Br^-$. In order to produce a cationic polymer with only one specific counter anion (e.g. hydrophilic counter anions like $Cl^-$, $Br^-$, $I^-$, $CH_3SO_3^-$, etc. or hydrophobic counter anions like $BF_4^-$, $CF_3SO_3^-$, $PF_6^-$, etc.), an anionic-exchange reaction is performed by dialysis or precipitation. As expected, all resulting polymers were found to be soluble in aqueous solutions when in the presence of hydrophilic anions.

Scheme 6

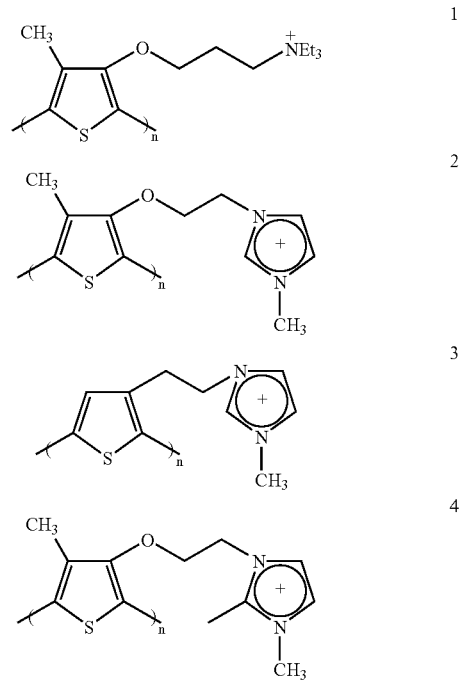

Figure 5:
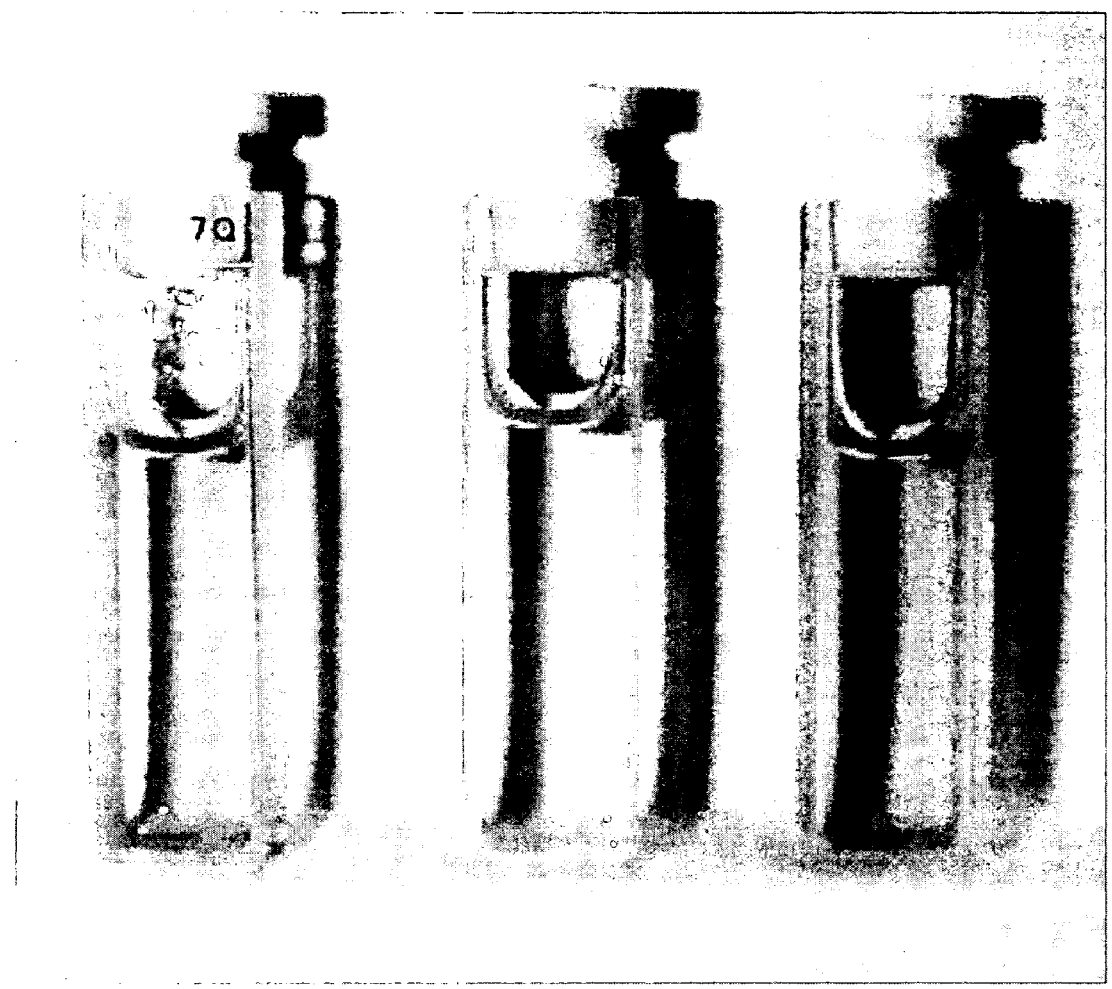
FIG. 5 shows a photograph of a polymer 2-oligonucleotide duplex (solution in the left tube was colored purple-red); a polymer 2-hybridized oligonucleotides triplex (solution in the middle tube was colored yellow); and a polymer 2 with partially hybridized oligonucleotides with two mismatches (solution in the right tube was colored pink).

As any water-soluble cationic polyelectrolytes, the polythiophene derivatives of the present invention can make strong complexes with negatively-charged oligomers and polymers.[17] This complexation results in the formation of complexes having specific optical properties. For instance, at 55° C., aqueous solutions (0.1 M NaCl or 10 mM Tris buffer/0.1M NaCl) of the cationic polymer 2 are yellow ($\lambda$max=397 nm). This absorption maximum at a relatively short wavelength is related to a random coil conformation of the polythiophene derivative.[6] After the addition of one equivalent (on a monomeric unit basis) of a given oligonucleotide (20-mers), the mixture becomes red ($\lambda_{max}$=527 nm) due to the formation of a so-called duplex. After 5 minutes of mixing in the presence of one equivalent of a complementary oligonucleotide, the solution becomes yellow ($\lambda_{max}$=421 nm) presumably due to the formation of a new complex (triplex) (FIGS. 1 and 5).

Figure 6:
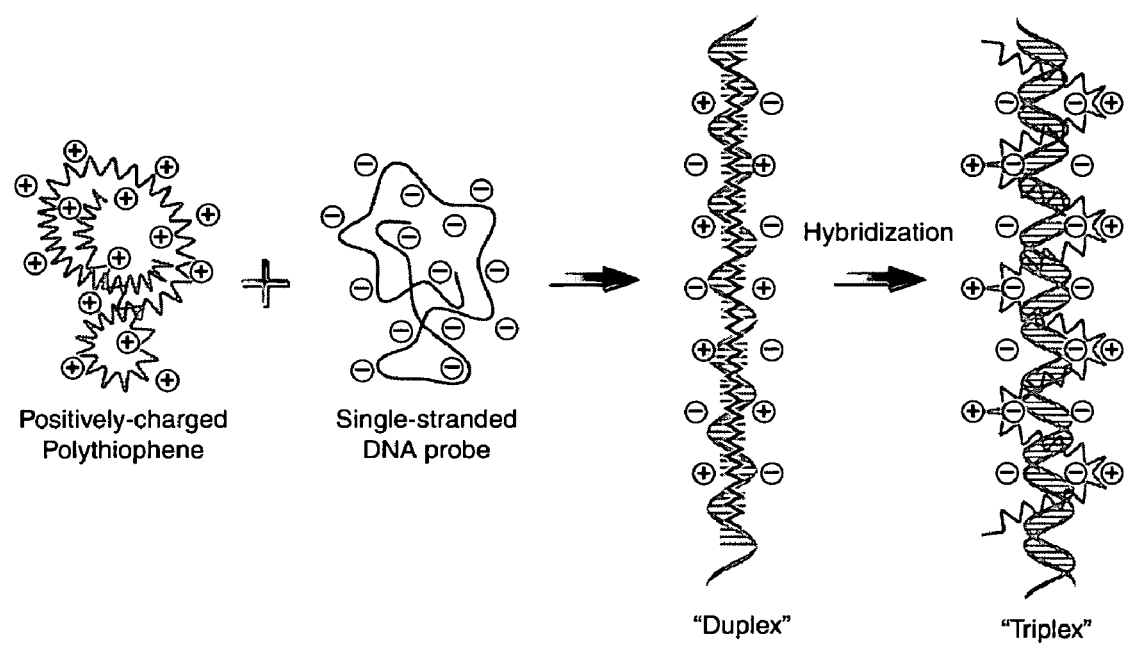
FIG. 6 shows the formation of a duplex and a triplex between polymer 2 and oligonucleotides.

A schematic description of these conformational transitions for both types of polyelectrolytes is given in FIG. 6.

Based on previous studies on thermochromic, solvatochromic and affinitychromic regioregular poly(3-alkoxy-4-methylthiophene)s,[6] it is believed that these calorimetric effects are made possible due to the different conformational structure of the conjugated polymer in the duplex (highly conjugated, planar conformation) compared to that observed in the triplex (less conjugated, non-planar conformation) and to a stronger affinity of the conjugated polymer for the double-stranded oligonucleotides (nucleic acids) ($1 \times 10^5$ $M^{-1}$) than that measured for single stranded oligonucleotides (nucleic acids) ($5 \times 10^4$ $M^{-1}$).

Figure 2:
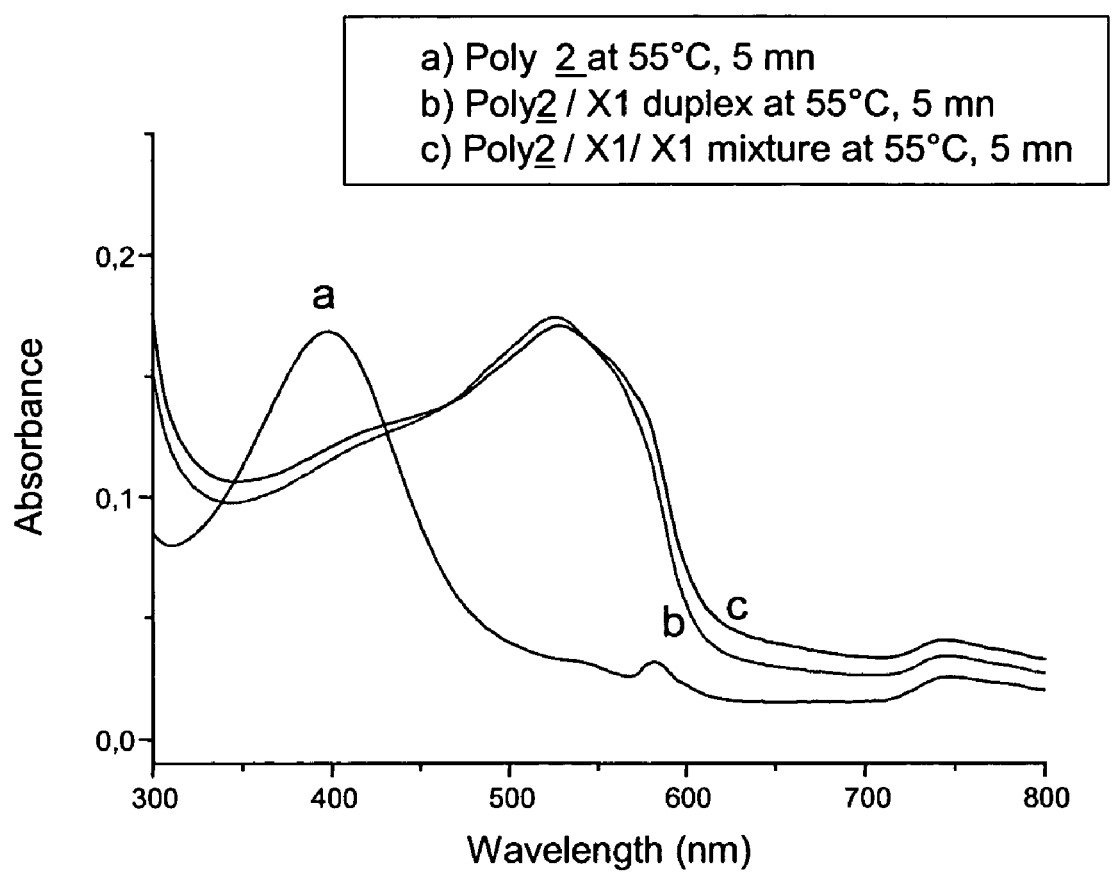
FIG. 2 shows the UV-visible absorption spectrum of a $2.4 \times 10^{-5}$ M (on a monomeric unit basis) solution of: a) polymer 2; b) polymer 2/X1 duplex; c) polymer 2/X1/X1 mixture, at 55° C. in 0.1M NaCl/H$_2$O.

In a control experiment it was demonstrated that the addition to the solution of an oligonucleotide identical to that of the capture probe results in no color change (FIG. 2).

Figure 13:
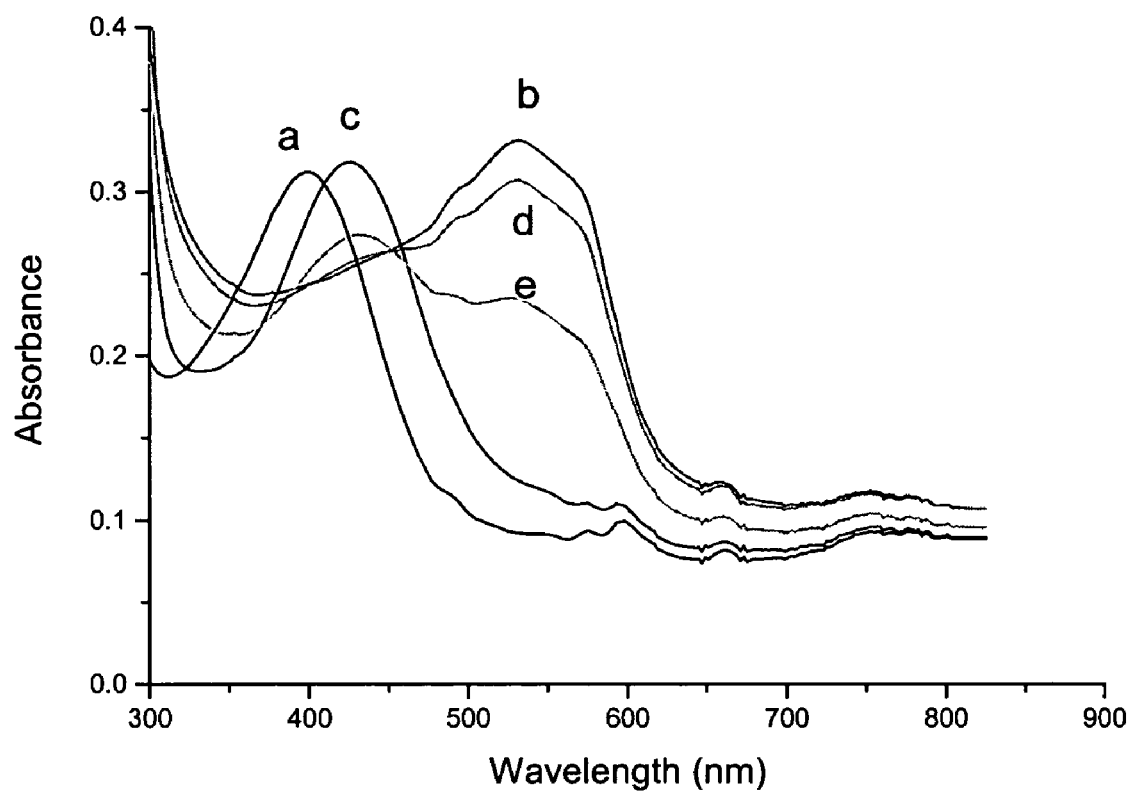
FIG. 13 shows the UV-visible absorption spectrum of a $2.4 \times 10^{-5}$ M (on a monomeric unit basis) solution of a) polymer 2, b) polymer 2/X1 duplex, c) polymer 2/X1/Y1 triplex, d) polymer 2/X1/Y2 mixture, and e) polymer 2/X1/Y3 mixture, at 55° C., in 0.1 M NaCl/H$_2$O. Capture probe X1: 5'CATGATTGMCCATCCACCA 3' and its perfect complementary target Y1: 3' GTACTMCTTGGTAGGTGGT 5' are a DNA oligonucleotide pair specific for *Candida albicans*; capture probe X2: 5' CATGATTGMGCTTCCACCA 3' and its perfect complementary target Y2: 3' GTACTAACTTCGAGGTGGT 5' are a DNA oligonucleotide pair specific for *Candida dubliniensis*; Y3: 3' GTACTMCTTCGTAGGTGGT 5' is a complementary target DNA oligonucleotide designed to have one mismatch with both the *C. albicans* and the *C. dubliniensis* capture probes.

In order to verify the specificity of these complexations, two pairs of complementary oligonucleotides (20-mers) differing by only 1 or 2 nucleotides were synthesized (Table 1) and carefully investigated. A slight but distinct change in the UV-visible absorption spectrum is observed in the case of the oligonucleotide target having 2 mismatches. Even with only one mismatch, it is possible to distinguish between a perfect and a non-perfect hybridization (FIG. 13). In this case, the calorimetric difference is mainly based on different kinetics of complexation, since similar yellow aqueous solutions are observed after 30–60 minutes of mixing at 55° C. However, it is possible to stop the hybridization reaction after 5 minutes of mixing, by placing the solutions at room temperature. Following these procedures, stable yellow and orange solutions are obtained (curves c and e) (FIG. 13). The detection limit of this calorimetric method is about $1 \times 10^{13}$ molecules of oligonucleotide (20-mers) in a total volume of 100 µL.

Figure 17:
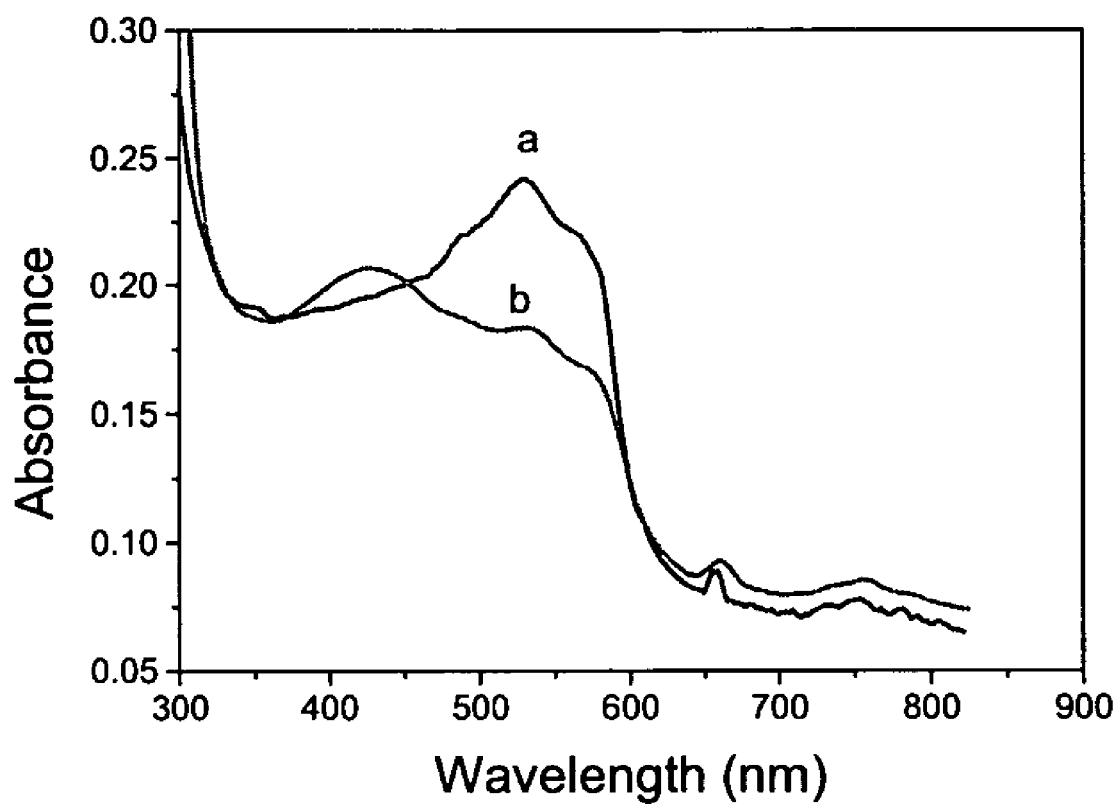
FIG. 17 shows the UV-visible absorption spectrum of a $2.4 \times 10^{-5}$ M (on a monomeric unit basis) solution of: a) polymer 1/X1 duplex; b) polymer 1/X1/Y1 triplex, at 55° C. in 0.1 M NaCl/H$_2$O.
Figure 18:
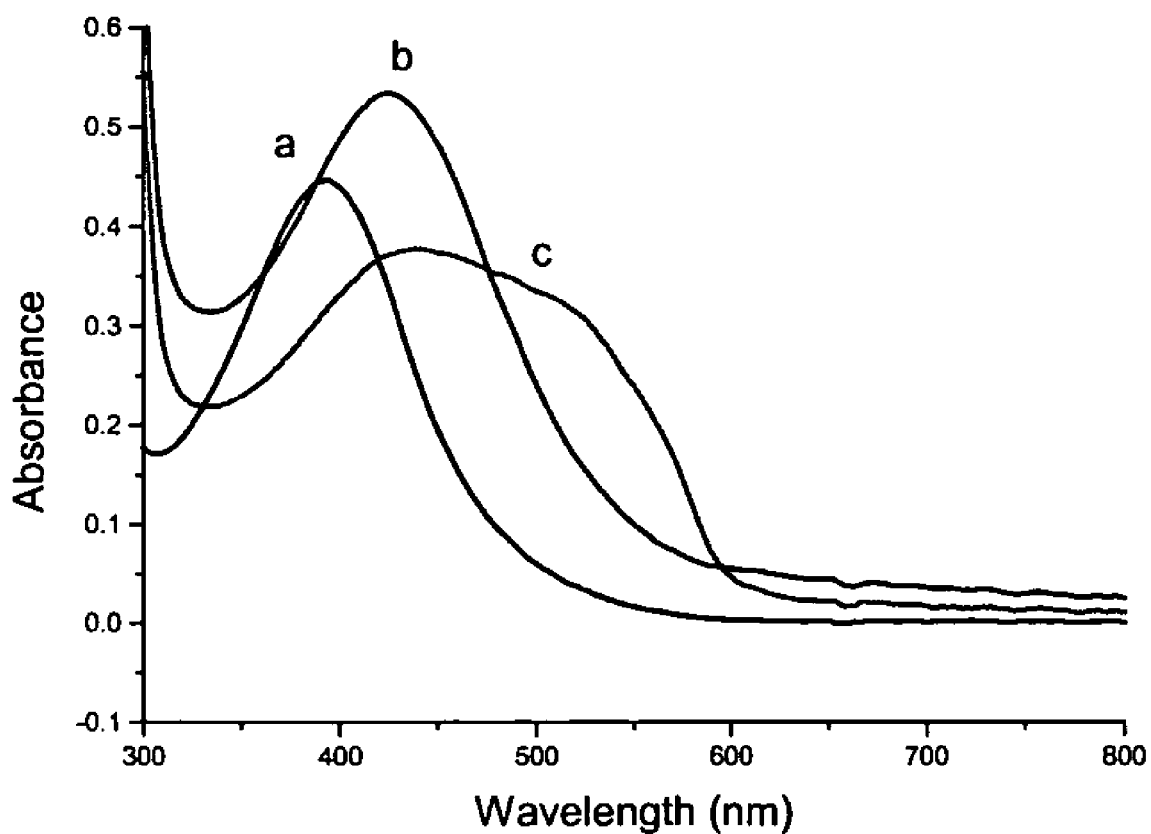
FIG. 18 shows the UV-visible absorption spectrum of a $2.4 \times 10^{-5}$ (on a monomeric unit basis) solution of: a) polymer 4; b) X1/Y1/polymer 4 triplex; c) X1/X1/polymer 4 mixture, at 25° C. in 0.1M NaCl/H$_2$O.
Figure 20:
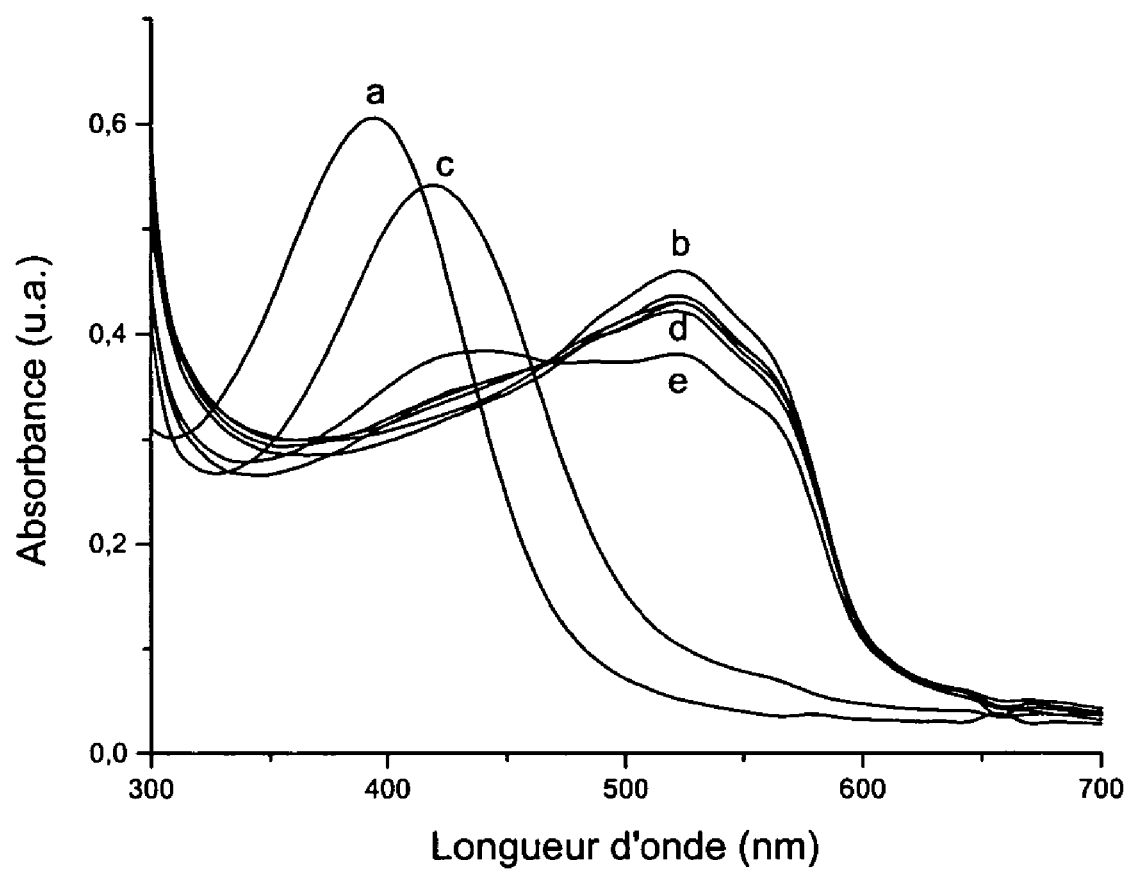
FIG. 20 shows the UV-visible spectroscopy spectrum of $7.9 \times 10^5$ M solutions in 0.1M NaCl and TE, at 55° C. of a) polymer 2; b) duplex (X1+polymer 2); c) triplex (X1+Y1+polymer 2); d) triplex with 2 mismatches (X1+5' TGGTG-GATGCATCAATCATG 3'), triplex with 3 mismatches (X1+5' TGGTGGATACATCAATCATG 3'), triplex with 5 mismatches (X1+5' TGGTGGAAACAACMTCATG 3'); e) triplex with 1 mismatch (X1+5' TGGTGGATGCTTCAAT-CATG 3').
Figure 21:
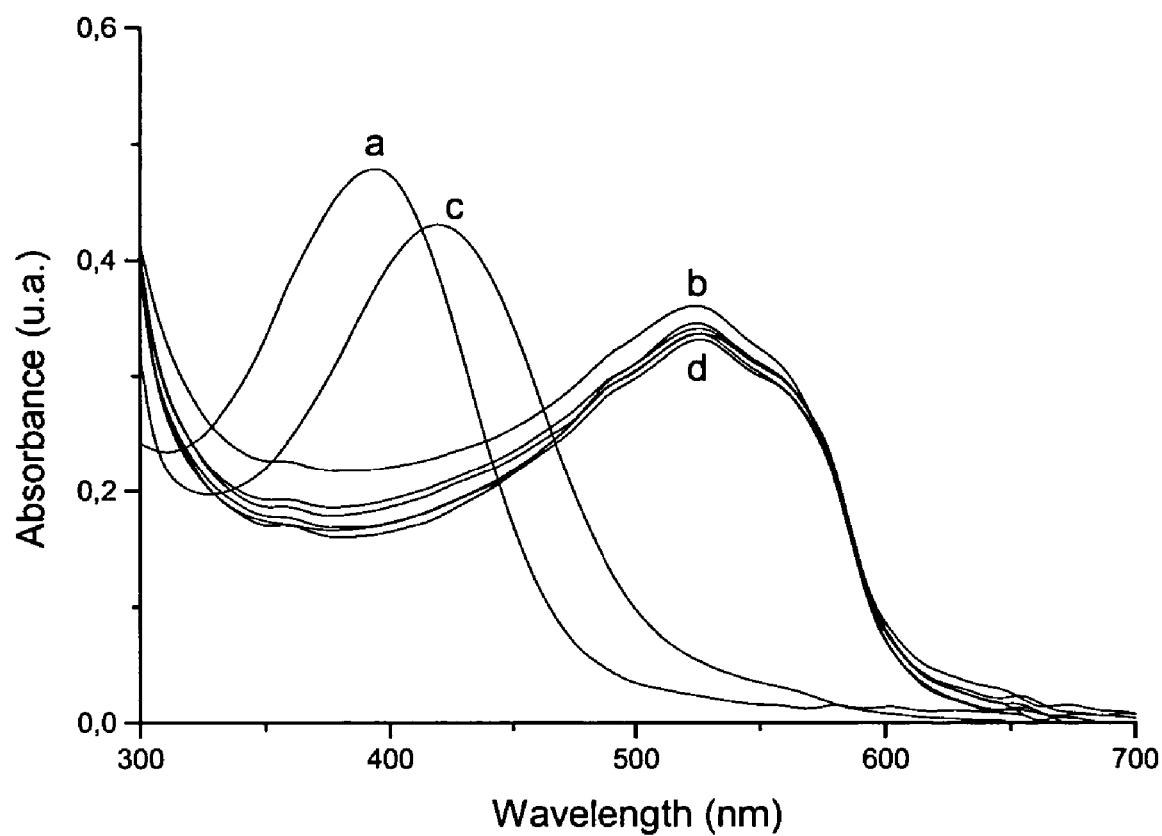
FIG. 21 shows the UV-visible spectroscopy spectrum of $7.9 \times 10^{-5}$ M solutions in 0.1M NaCl and TE, at 55° C. of a) polymer 2; b) duplex (X1+polymer 2); c) triplex (X1+Y1+polymer 2); d) triplex with 2 mismatches (X1+Y2), (X1+5' TGGTAGATGCTTCAATCATG 3'), (X1+5' TGGTGGT-TGCTTCAATCATG 3'), (X1+5' TGGTGGATGCTTT-TAATCATG 3'), (X1+5' TGGTGGATGCTTCATTCATG 3'), (X1+5' TGGTGGATGCTTCAATTATG 3').

Very similar results have been obtained for polymer 1 (FIG. 17) and polymer 4 (FIG. 18) and various oligonucleotides. FIG. 20 shows the UV-Visible absorbance spectrum of polymer 2 when using target oligonucleotides ranging from 0 to 5 mismatches. FIG. 21 illustrates the UV absorbance results of polymer 2 using the target oligonucleotide always having two mismatches at different positions. These results show that the polymer can discriminate between perfectly matched and mismatched hybrids, independently of the nature of the mismatched nucleotide bases, and independently of the position or the length of the mismatches. Moreover, it is even possible to discriminate a single mismatch from multiple mismatches.

TABLE 1

Synthetic oligonucleotides to study the specificity of hybridization.

| Oligonucleotides specific for *Candida albicans* | Oligonucleotide specific for *Candida dubliniensis* |
| --- | --- |
| X1<br>5'<br>CATGATTGAACCATCCACCA<br>3'<br>Y1<br>3'<br>GTACTAACTTGGTAGGTGGT<br>5' | X2<br>5'<br>CATGATTGAAGCTTCCACCA<br>3'<br>Y2<br>3'<br>GTACTAACTTCGAAGGTGGT<br>5' |
| Y3 (designed to have one mismatch wit X1 and X2)<br>3' GTACTAACTTCGTAGGTGGT 5' | |

The concentration of a particular sequence region of DNA can be amplified by using a polymerase chain reaction (PCR), and the present colorimetric method can be extended to these PCR products. Indeed, the introduction of the polymerase chain reaction (PCR) has solved the problem of detecting small amounts of DNA and the polymers of the present invention can be used in the identification of PCR products. UV spectroscopic results in the absorbance range of 430–530 nm (FIG. 4) have illustrated the specific optical detection of *Candida albicans* and *Candida dubliniensis* amplicons, which differ by only 2 nucleotides, by a polymer 2/X1 duplex. Such detection was carried out in 45 minutes directly from a PCR product at a concentration normally generated in a 100 µL PCR volume (ca. $3 \times 10^{12}$ copies). Experimental details on PCR and choice of target sequences for identification of *Candida* are provided in a co-pending patent application (PCT/CA00/01150).

Figure 19:
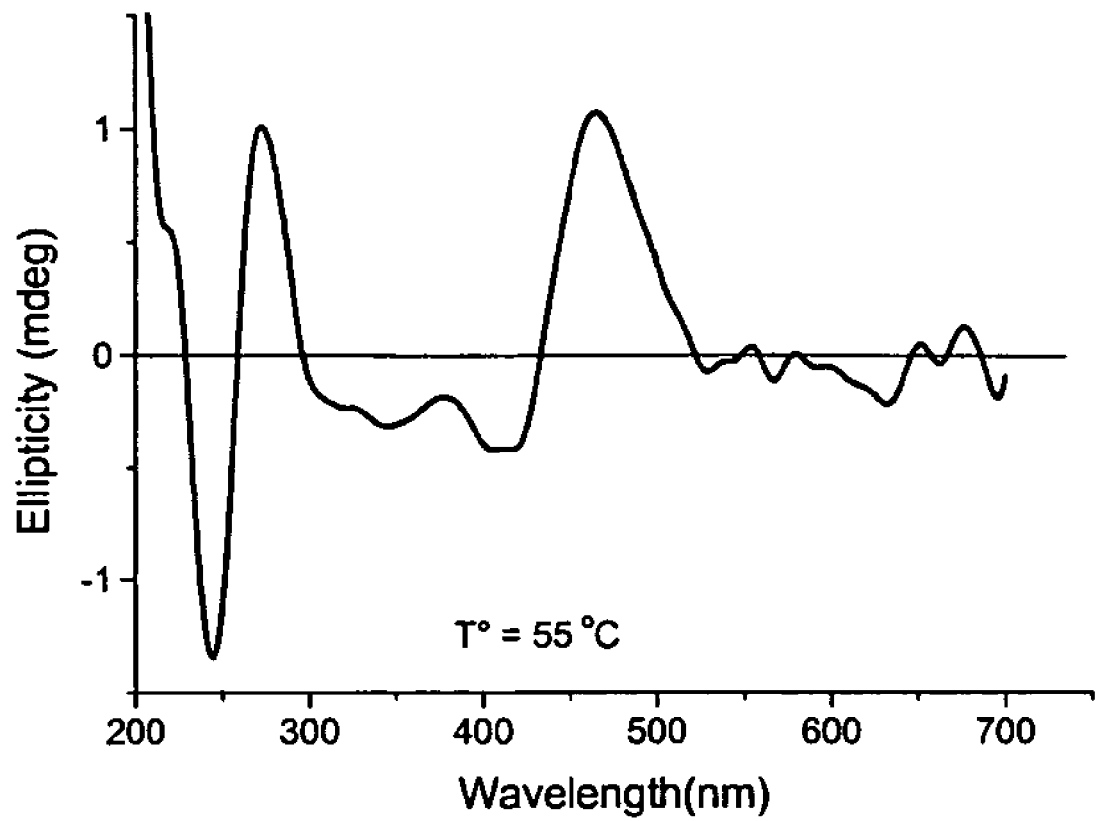
FIG. 19 shows the circular dichroism of a $1.2 \times 10^{-4}$ M (on a monomeric unit basis) solution of polymer 3/X1/Y1 triplex at 55° C. in 10 mM Tris buffered solution containing 0.1M NaCl.

In addition, as shown in FIG. 19, circular dichroism (CD) measurements reveal an optical activity for polymer 3 in its random coil, a bisignate CD spectrum centered at 420 nm in the triplex, characteristic of a right-handed helical orientation of the polythiophene backbone. Such a right-handed helical structure is compatible with binding of the polymer to the negatively-charged phosphate backbone of DNA. The thermal stability study by UV or CD measurements shows a different thermal stability between a duplex and a triplex, and this property could be extremely useful for more stringent washing conditions.

Figure 7:
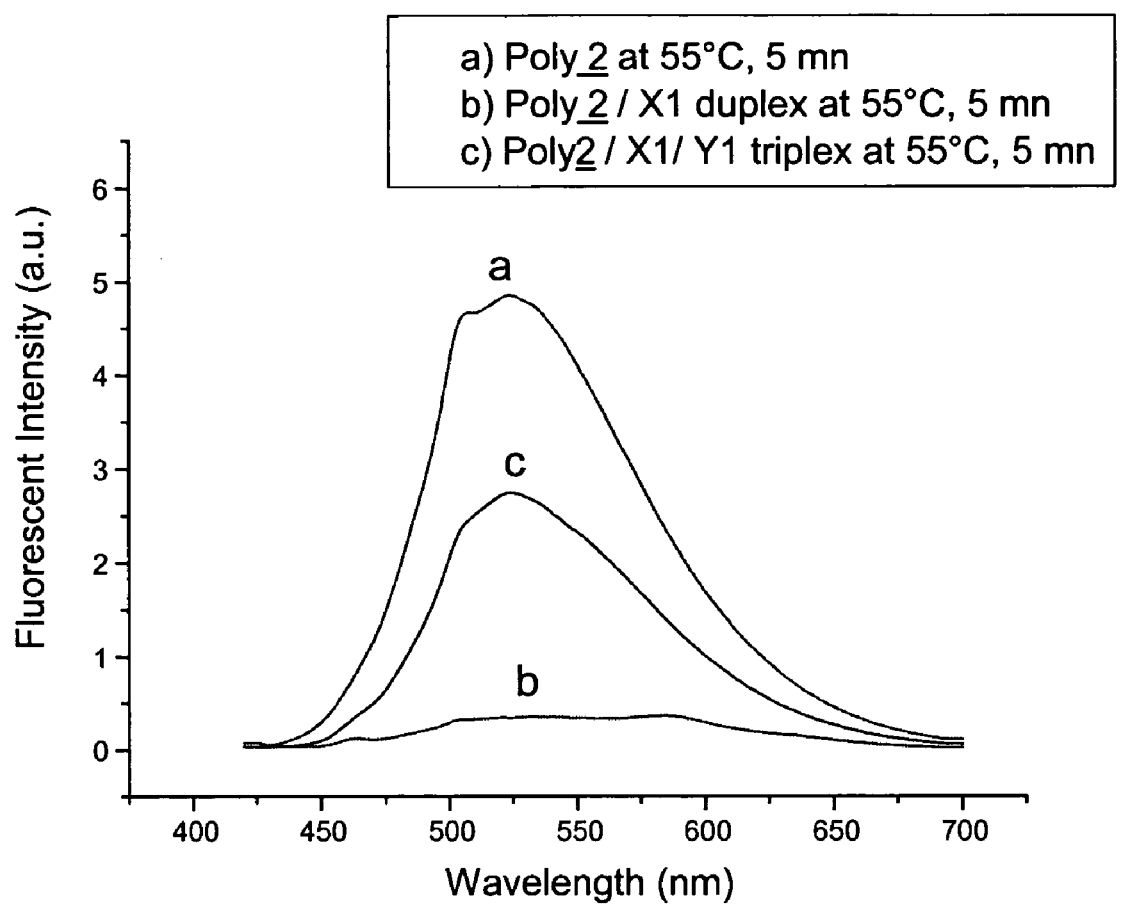
FIG. 7 shows the fluorescence intensity during specific hybridization.
Figure 8:
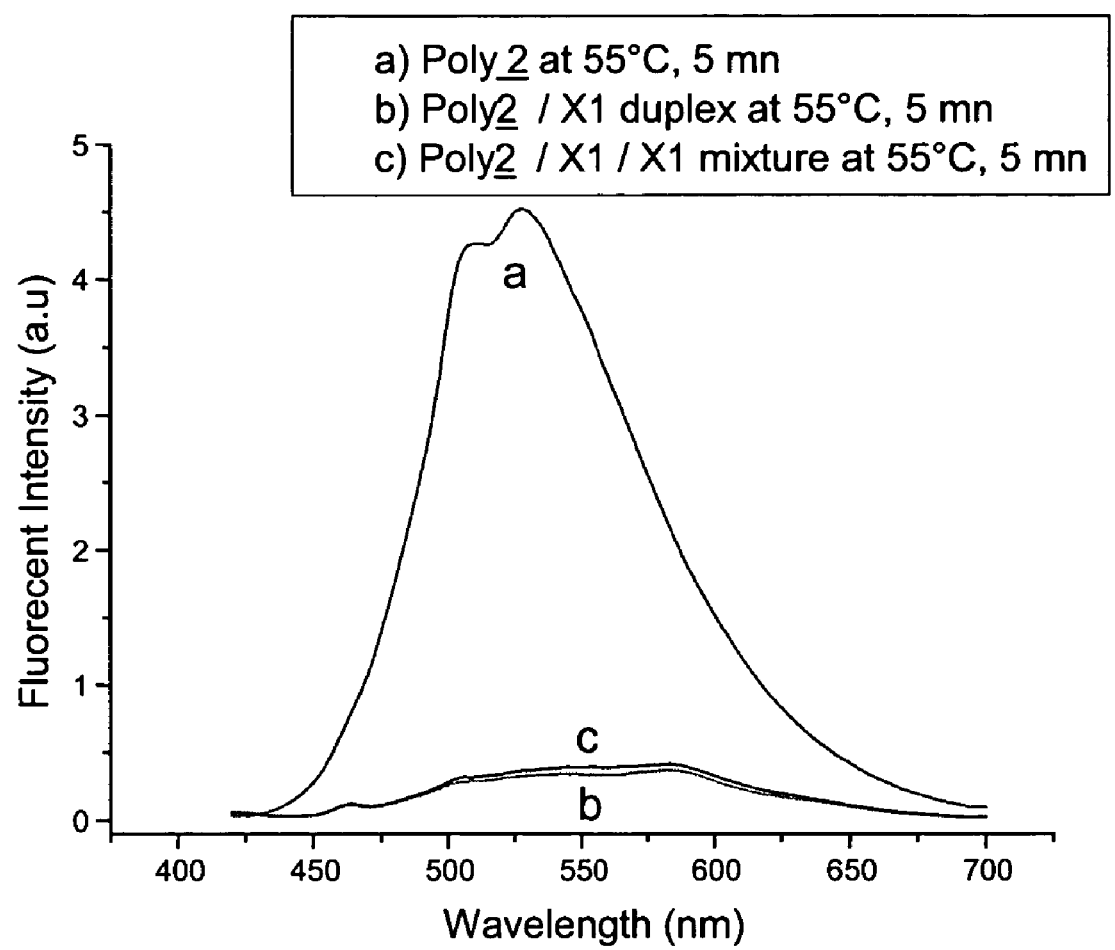
FIG. 8 shows the fluorescence intensity during non hybridization.

A fluorometric detection of oligonucleotide hybridization is also possible based on the difference in the fluorescence quantum yield of the positively-charged poly(3-alkoxy-4-methylthiophene) in the random coil (the isolated state) or in the aggregated state.[16] For instance, at 55° C., the yellow appearance of polymer 2 is fluorescent (quantum yield of 0.03) but upon addition of one equivalent of a negatively-charged oligonucleotide, the intensity of the emission spectrum is strongly decreased (quenched). In the case of perfect hybridization, the polymeric triplex gives a stronger emission (FIG. 7). Upon addition of the same oligonucleotide, no hybridization occurs and the solution does not show any change in fluorescent intensity (FIG. 8). Using a laser as the excitation source, very low limits of detection are obtained. It is possible to detect the presence of as few as $3 \times 10^6$ molecules of the complementary oligonucleotide (20-mers) in a volume of 200 µL, which corresponds to a concentration of $2 \times 10^{-14}$ M. Moreover, by covalently attaching the oligonucleotide to a fluorescent-conjugated polymer, or by using an optimized fluorescence detection scheme based on a high intensity blue diode (excitation source) and a non-dispersive, interference filter-based system, an even more sensitive and more specific detection capability is achieved.

Figure 9:
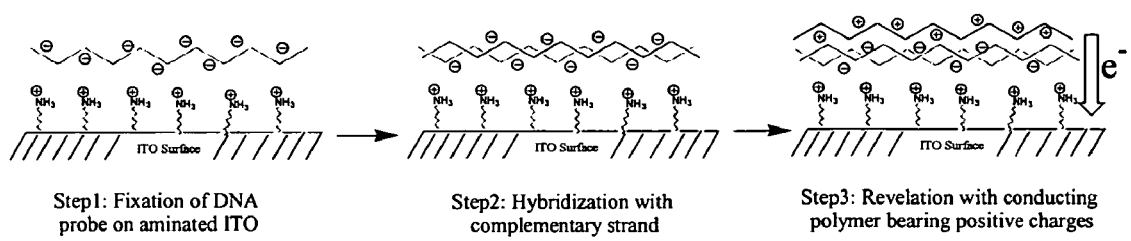
FIG. 9 shows the different steps involved in the electrochemical detection of DNA hybridization.

The electrochemical properties of polymers 1 and 2 can be used for the detection of DNA hybridization in aqueous solutions, as shown in FIG. 9.[8,10] Using the layer by layer deposition techniques,[25,26] the first step required the binding of a capture probe composed of single-stranded oligonucleotide X1 to an ammonium-functionalized indium tin oxide (ITO) surface.[18,27] After rinsing with pure water, the modified electrode so-obtained was dipped and hybridized in the presence of a complementary oligonucleotide Y1. The resulting electrode was revealed with an aqueous solution of positively-charged polymer 1 or 2 ($10^{-4}$ M on a monomeric basis), which provides a signal that is a function of the amount of DNA present on the surface. As a control experiment, an aqueous solution of oligonucleotide X1 was added to the X1 modified ITO electrode, and then transferred into an aqueous solution of polymer 1 or 2. In this way, these polymers serve as "mass transducers" for the oligonucleotide present in the sample.

Figure 10:
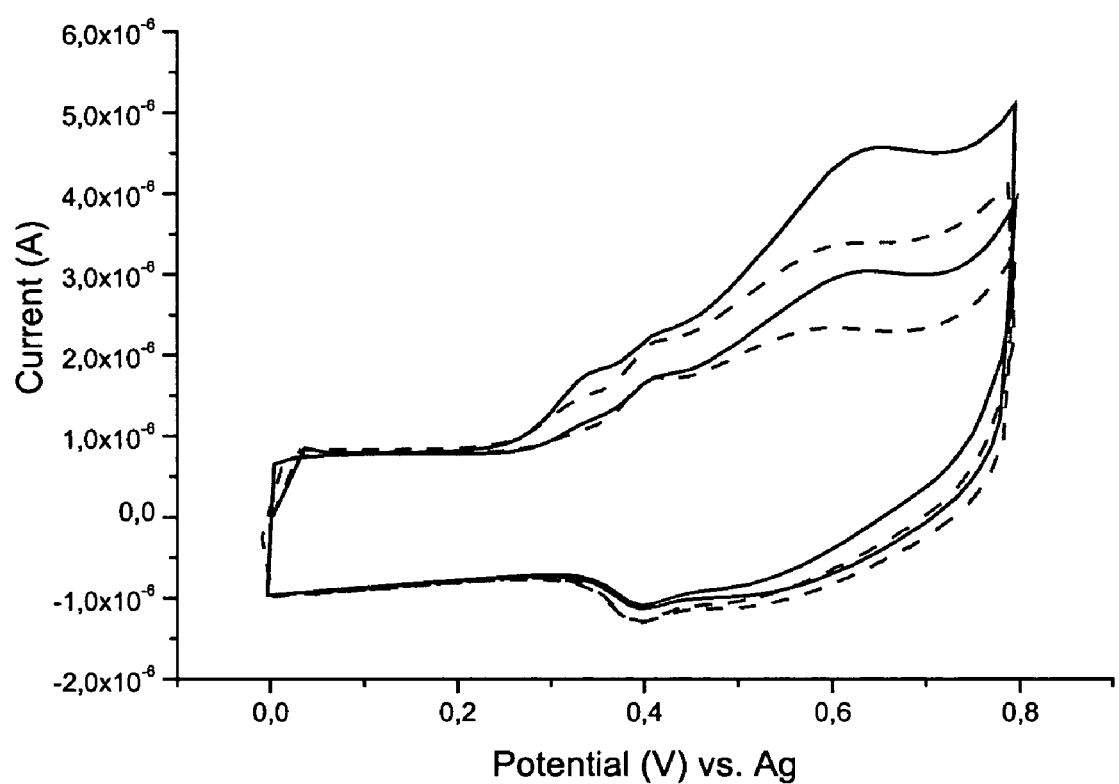
FIG. 10 shows the Cyclic voltammogram of polymer 1 onto an ITO modified electrode (S=50 mm$^2$) in the case of perfect hybridization (straight line) and in the case of a control blank (dashed line) in 0.1 M NaCl/H$_2$O. Scan rate 100 mV/s (two successive cycles).
Figure 11:
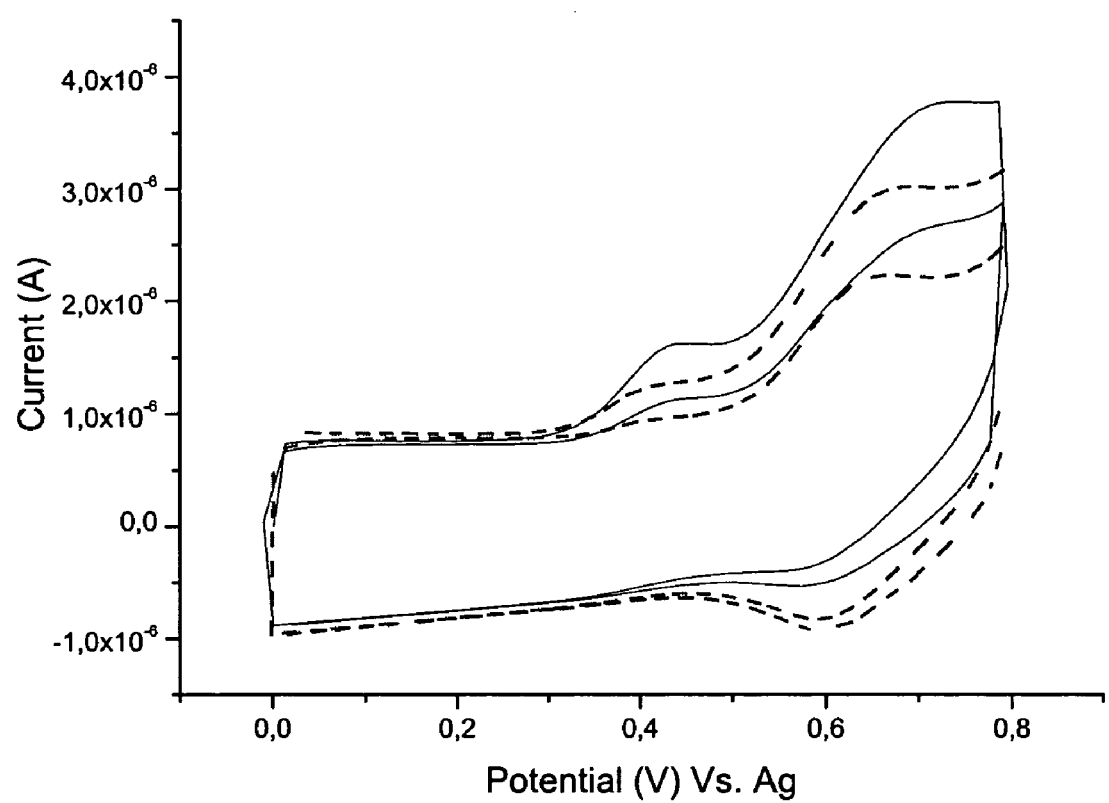
FIG. 11 shows the Cyclic voltammogram of polymer 2 onto an ITO modified electrode (S=50 mm$^2$) in the case of perfect hybridization (straight line) and in the case of a control blank (dashed line) in 0.1 M NaCl/H$_2$O. Scan rate 100 mV/s (two successive cycles).

The detection of DNA hybridization is further demonstrated by the following two examples using different cationic poly(3-alkoxy-4-methylthiophene)s (polymers 1 and 2). The so-obtained results are illustrated in FIGS. 10 and 11.

In both cases, the maximum anodic current is more important in the case of perfect hybridization as compared to the blank control. In addition, a shift to a higher potential (ca. 40–50 mV) is observed when specific hybridization occurs (38 mV for polymer 4 as compared to 52 mV for polymer 2). The higher oxidation current can be explained by the stronger affinity of the polymers for double-stranded oligonucleotides, whereas the positive shift of oxidation potential is explained by the formation of a less conjugated structure in the case of specific hybridization. This is in agreement with previous optical measurements.

An assay using a smaller electrode [S(surface)=10 mm$^2$] has allowed the detection of $2\times10^{11}$ molecules of oligonucleotide (20-mers). This very simple electrochemical methodology is already more sensitive, by two orders of magnitude, than the best results obtained with electrochemical methods using oligonucleotide-functionalized conjugate polymers.[10] Clearly, by decreasing the size of the electrodes and by increasing the size of the target molecules, much lower detection limits should be obtained.

In order to further enhance the specificity of the detection, the oligonucleotide probe can be covalently attached to the polythiophene derivatives The detection of DNA sequences can also be carried out electrochemically as shown below in Scheme 7.

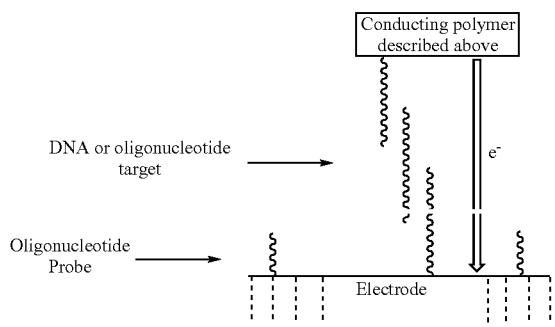

Scheme 7

Figure 12:
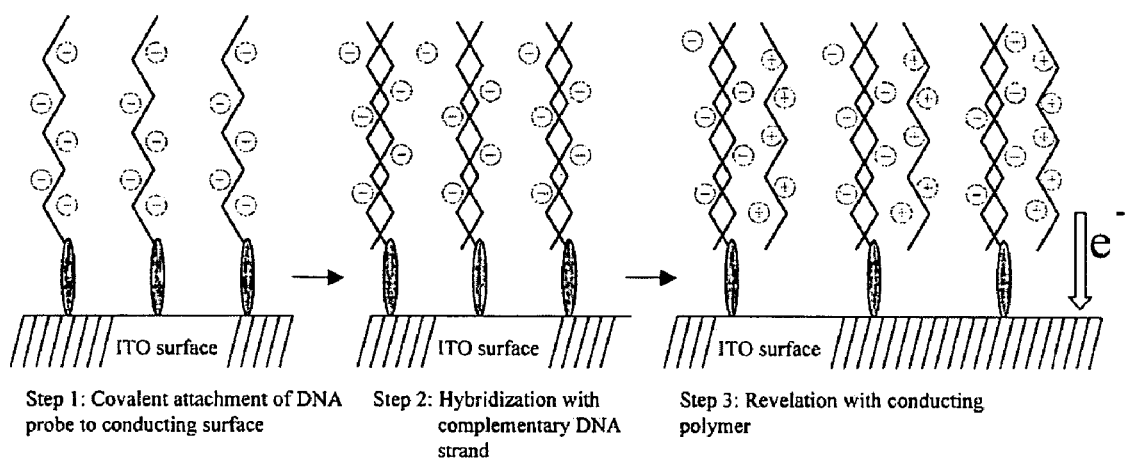
FIG. 12 shows the covalent attachment of a DNA probe onto a conducting surface, its subsequent hybridization with a complementary DNA strand and its revelation with a conducting polymer.

The DNA probes can be covalently fixed to a conductive surface (FIG. 12). This allows for the linking of a larger number of DNA probes to the surface, improving the specificity and detection limit for a small surface.

The first step involves the modification of the conductive substrate (ITO, SnO$_2$, gold, doped silicon or other conductive substrate) by the covalent attachment of a single-stranded DNA probe. The complementary DNA strand is hybridized and the polymer is captured on the hybridized probe. The observed electrochemical signal is different for a hybridized probe (ds-DNA) versus a non-hybridized probe (ss-DNA). A linker can be used to attach the DNA probe to the conductive surface. The end groups of the linker are such that one end readily reacts with the conductive substrate to form a covalent bond, whereas the other end readily reacts with an "end-modified" (SH, NH$_2$, COOH, etc.) DNA probe, with or without a spacer (carbon$_{24}$) between the reactive function and the DNA.[19,20,21] The end group of the linker that reacts with the conductive substrate's surface can be a silane derivative, such as an alkoxysilane, or a chlorosilane. The other end group of the linker can be composed of an aldehyde, a carboxylic acid, a primary amine, a succinimide ester moiety or other functional groups capable of reacting with "end-modified" DNA probes, that is, DNA probes having specific end groups, resulting in the formation of covalent bonds with or without the help of coupling agents.

The immobilization of an oligonucleotide by means of a thiol group can be carried out through its 3' or 5' terminal group. Accordingly, DNA was immobilized onto an ITO surface following the literature procedure for immobilizing DNA on a glass surface.[28,29,30]

It is also possible to link "end-modified" DNA probes to various other surfaces such as gold or other metals and metal oxides.[22] Non-metallic surfaces such as beads, glass slides, optical fibers or any other suitable non-metallic solid support, are also possible. The immobilization of DNA onto a gold surface is accomplished following known published techniques, and the density of the attached probes can vary depending on the concentration and reaction times.[31,32] The hybridization efficiency can be optimized by heating the substrate before adding the complementary strand.[31,33] Polymer deposition can be optimized by dipping the substrate vertically into a polymer solution, and by varying the salt concentration and the temperature of the polymer solution. The washes can be further optimized to limit the contribution of the polymer with the non-hybridized probe.

The signal observed for a triplex should be stronger than that observed for a duplex, with possibly a small shift towards higher potentials when hybridization occurs. The amount of DNA is higher in the case of a triplex, which implies the presence of a higher amount of negative charges. It is suspected that there might be two equivalents of polymer (positive charge) binding in the case of a triplex. Moreover, in the case where only one equivalent of polymer is bound to DNA, the polymer on a non-hybridized probe (ss-DNA) is more easily washed off, as compared to a polymer bound to DNA on a hybridized probe (ds-DNA), since it is less stable at high salt content or elevated temperatures. By washing off essentially all of the polymer from the duplex while leaving the triplex intact, a signal coming directly from the triplex (hybridized probe+polymer) is assured. Finally, targets having mismatches will give a different signal and possibly a lower current, due to less perfect hybridization.

Figure 14:
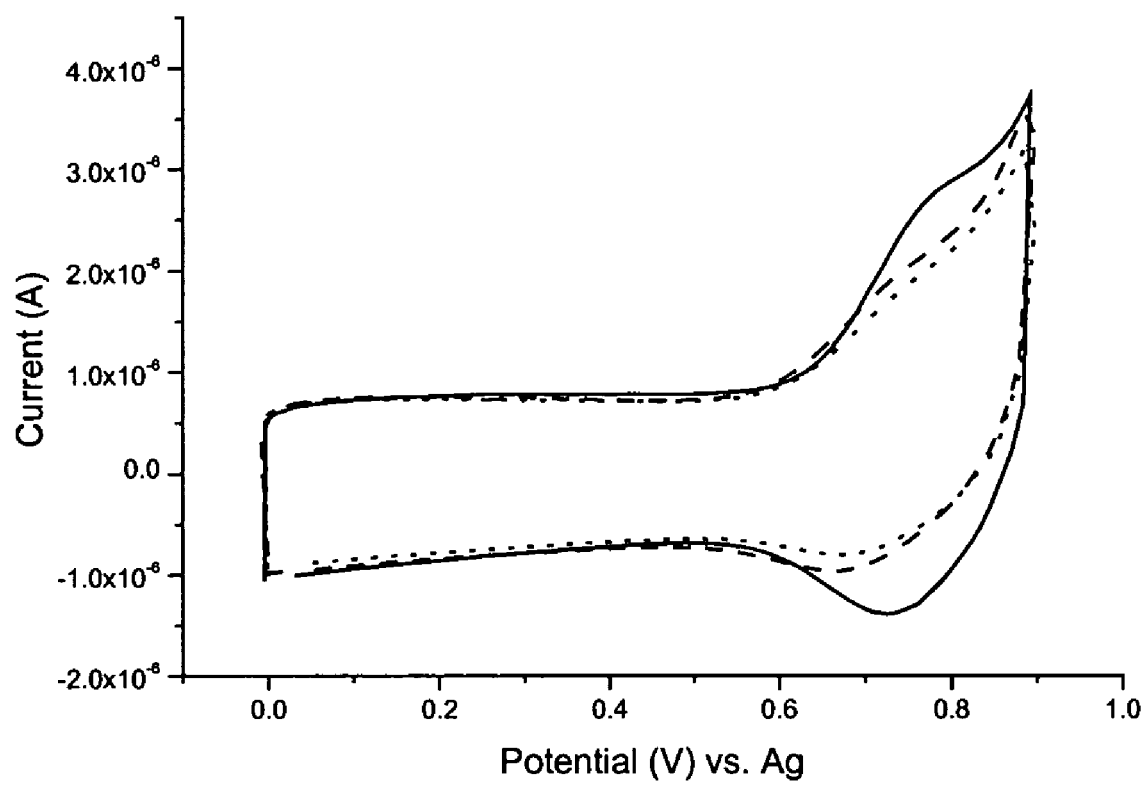
FIG. 14 shows a cyclic voltammogram of polymer 2 (SH-carbon$_{24}$-DNA with polymer 2) bound to an ITO modified electrode (50 mm$^2$) in the case of perfect hybridization (X1/Y1; full line) and in the case of two control blanks (X1/X1, dotted line and X1, dashed line) in 0.1 M NaCl/H$_2$O using a scan rate of 100 mV/s.
Figure 15:
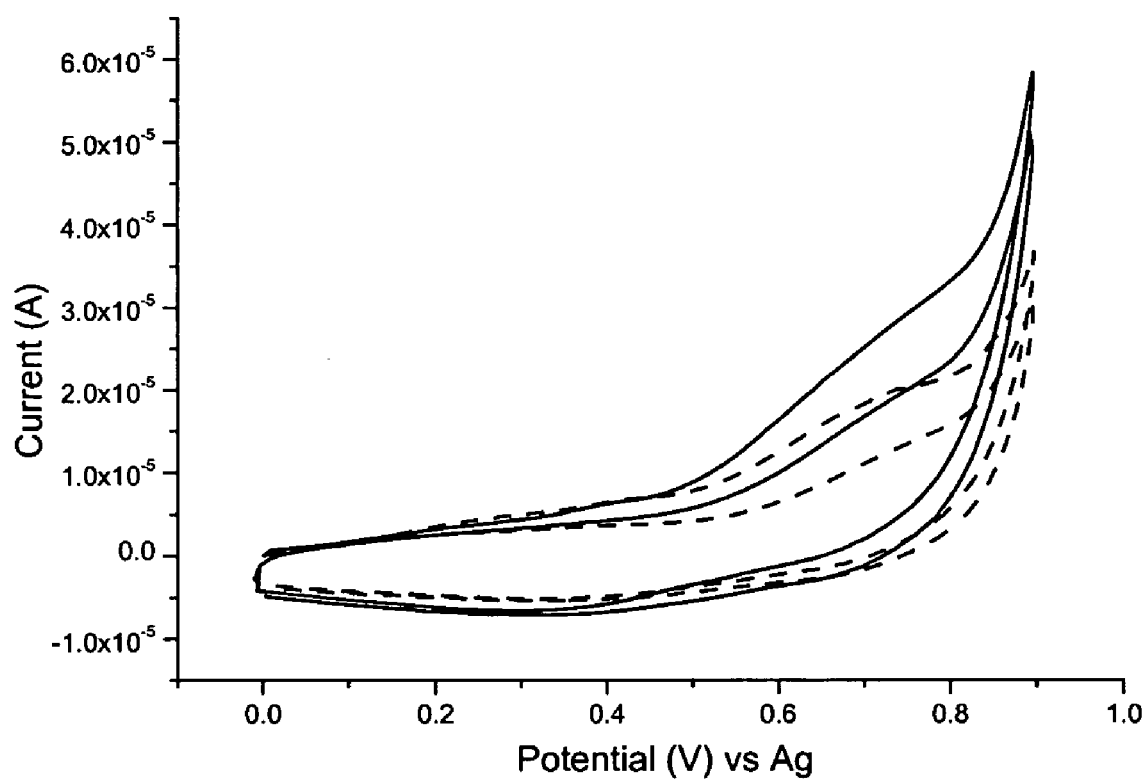
FIG. 15 shows a cyclic voltammogram of polymer 2 (SH-carbon$_{24}$-DNA with polymer 2) bound to a gold modified electrode (50 mm$^2$) in the case of perfect hybridization (X1/N1; full line) and in the case of a control blank (X1, dashed line) in 0.1 M NaCl/H$_2$O. The electrodes were submitted to a −0.4 V potential for 10 minutes before scanning; the scan rate used was 50 mV/s.
Figure 16:
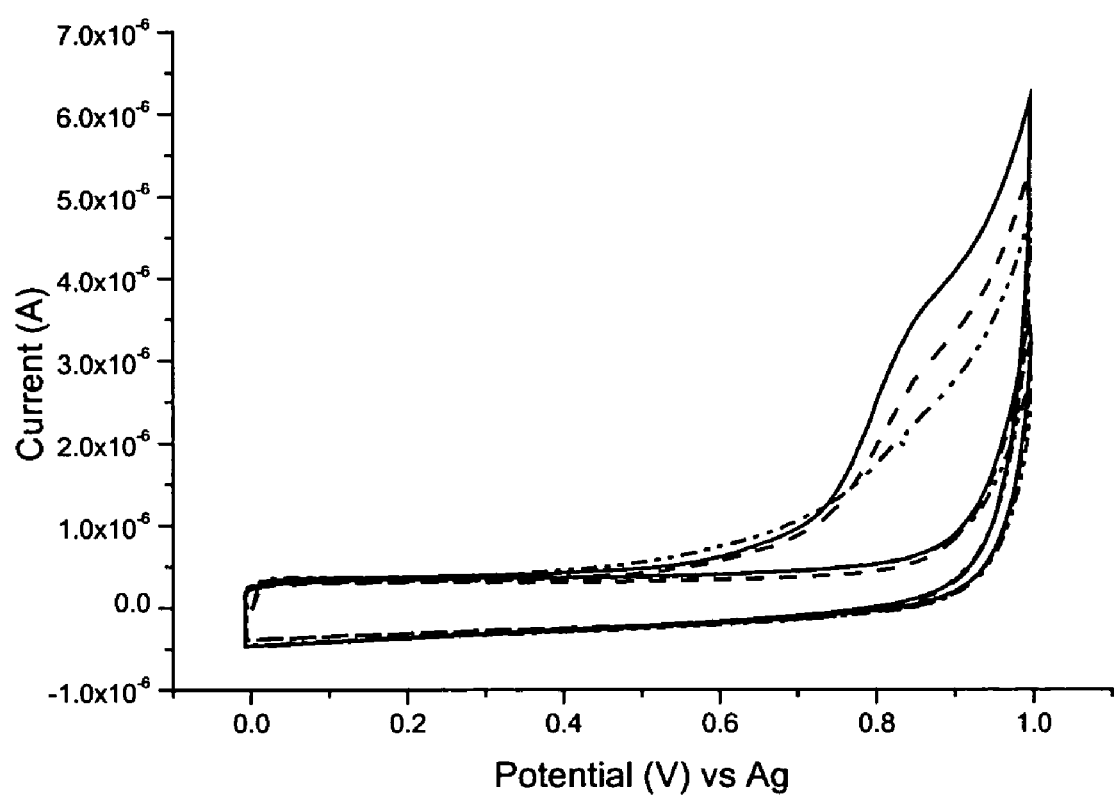
FIG. 16 shows a cyclic voltammogram of polymer 3 (SH-carbon$_{24}$-DNA with polymer 3) bound to an ITO modified electrode (50 mm$^2$) in the case of perfect hybridization (X1/N1; full line) and in the case of two control blanks (X1, dashed line and silanized ITO (no DNA), dash-dotted line) in 0.1 M NaCl/H$_2$O using a scan rate of 50 mV/s.

The electrochemical detection of DNA hybridization is further demonstrated by using polymer 2 and polymer 3, as illustrated in FIGS. 14–16.

Experimental Section

EXAMPLE 1

General Procedure for the Aromatic Nucleophilic Substitution on Thiophene; Synthesis of Compound 3

Sodium hydride (0.4 g, 15 mmol) was added between 0 and 10° C. under nitrogen to a solution of N,N-diethylpropanolamine (2.0 g; 15.2 mmol) in 50 mL of DME, and the resulting mixture stirred at ambient temperature for 20 minutes. 3-Bromo-4-methyl thiophene (2.0 g, 11.3 mmol) dissolved in 20 mL of DME (20 mL) and CuI (1.07 g, 5.65 mmol) were then added to the reaction mixture. The mixture was subsequently stirred overnight at 95° C., while under nitrogen, diluted with methylene chloride and filtered. The organic phase was washed three times with water, dried over MgSO$_4$ and evaporated. The crude product was purified by chromatography on silica gel using CH$_2$Cl$_2$ as the eluent, followed by the use of MeOH.

Compound 3: Yield 26%; $^1$H NMR (CDCl$_3$) δ: 1.04 (t, 6H); 1.93 (m, 2H); 2.09 (s, 3H); 2.57 (m, 6H), 3.97 (t, 2H); 6.14 (d, 1H); 6.81 (d, 1H); $^{13}$C NMR (CDCl$_3$) δ: 11.69; 12.50; 26.84; 46.91; 49.26; 68.19; 95.88; 119.57; 129.05; 156.04; MS m/e: Calcd. For C$_{12}$H$_{21}$N$_0$O$_1$S$_1$; 227.1344; Found: 227.1347.

EXAMPLE 2

General Procedure for Quaternization Reaction: Synthesis of Monomer 1

1-Bromoethane (6 mL, 80.4 mmol) was added to a solution of compound 3 (0.49, 1.8 mmol) in 60 mL of acetonitrile. The reaction mixture was stirred at 70° C. under nitrogen for 3 days. After evaporation of the acetonitrile, the crude product was crystallized from ethyl acetate as a colorless powder.

Monomer 1: Yield 100%; m.p. 145–147° C.; $^1$H NMR (CDCl$_3$) δ: 1.41 (t, 9H); 2.06 (s, 3H); 2.31 (m, 2H); 3.57 (m, 8H), 4.12 (t, 2H); 6.24 (d, 1H); 6.84 (d, 1H); $^{13}$C NMR (CDCl$_3$) δ: 7.87; 12.61; 22.55; 53.61; 54.66; 65.80; 97.18; 120.28; 128.26; 154.77.

EXAMPLE 3

Synthesis of Monomer 2

1-Methyl-imidazole (1.0 mL, 12.3 mmol) was added to a solution of product 4 (0.54 g, 2.46 mmol) dissolved in CH$_3$CN (35 mL). The resulting reaction mixture was stirred at 70° C. for two days. After evaporation of the solvent, the crude product was washed twice with warm ethyl acetate and twice with diethyl ether at room temperature to provide monomer 2 as a pure white solid compound.

Monomer 2: Yield 88%;. 92–94° C.; $^1$H NMR (CDCl$_3$) δ: 2.05 (s, 3H); 4.09 (s, 3H); 4.38 (t, 2H); 4.90 (t, 2H), 6.27 (d, 1H); 6.82 (d, 1H); 7.63 (s, 1H); 7.68 (s, 1H); 10.24 (s, 1H); $^{13}$C NMR (CDCl$_3$) δ: 12.81; 36.76; 49.36; 68.01; 97.92; 120.68; 123.26; 123.30; 128.35; 137.51; 154.23.

EXAMPLE 4

Synthesis of Monomer 3

Methanesulfonyl chloride (2.4 mL; 31.2 mmol) was added dropwise to a solution of 3-thiopheneethanol (2.0 g; 15.6 mmol) and triethylamine (4.3 mL; 31.2 mmol), in dichloromethane (50 mL). The reaction mixture was stirred at room-temperature for two hours. The organic phase was washed with a NaHCO$_3$ solution, followed by several washings with water, and was finally dried with MgSO$_4$ and concentrated. The crude product was purified by silica gel chromatography using CH$_2$Cl$_2$/hexane (1/1) as the eluent to yield compound 6 (59%); $^1$H NMR (300 MHz, CDCl$_3$, 25° C., TMS): δ=2.87 (s, 3H); 3.08 (t, 2H); 4.40 (t, 2H); 6.98 (d, 1H); 7.09 (d, 1H); 7.29 (dd, 1H). $^{13}$C NMR (300 MHz, CDCl$_3$, 25° C., TMS): δ=29.99; 37.19; 69.59; 122.24; 125.98; 127.98; 136.44.

1-Methyl imidazole (0.4 g; 4.85 mmol) was added to a solution of compound 6 (0.2 g; 0.97 mmol) in toluene (20 mL). The reaction mixture was stirred at 94° C. for two days. Following evaporation of the solvent, the crude product was washed with warm ethyl acetate to yield monomer 3 as a liquid.

Monomer 3: Yield (95%); $^1$H NMR (300 MHz, CDCl$_3$, 25° C., TMS): δ=2.72 (s, 3H); 3.19 (t, 2H); 3.90 (t, 2H); 4.49 (t, 2H); 6.95 (d, 1H); 7.06 (d, 1H); 7.24 (m, 2H); 7.33 (s, 1H); 9.68 (s, 1H). $^{13}$C NMR (300 MHz, CDCl$_3$, 25° C., TMS): δ=30.77; 36.10; 39.67; 50.06; 122.24; 122.81; 123.01; 126.46; 127.66; 136.08; 137.80.

EXAMPLE 5

Synthesis of Monomer 4

The quaternization reactions were carried out following the procedure described in example 3.

Monomer 4: Yield 85%; $^1$H NMR (300 MHz, CDCl$_3$, 25° C., TMS): δ=2.02 (s, 3H); 2.89 (s, 3H); 3.96 (s, 3H); 4.39 (t, 2H); 4.85 (t, 2H); 6.27 (d, 1H); 6.83 (d, 1H); 7.57 (d, 1H); 7.96 (d, 1H).

EXAMPLE 6

General Procedure for the Chemical Polymerization: Synthesis of Polymer 1

To a solution of iron trichloride (0.94 g, 5.8 mmol) in chloroform (23 mL) under nitrogen, a solution of monomer 1 (0.487 g, 1.4 mmol) in chloroform (15 mL) was added dropwise. The mixture was stirred at room temperature for a period of 2 days. The reaction mixture was evaporated to dryness and the crude product washed quickly with methanol, and dissolved in excess of acetone, and precipitated by the addition of an excess of tetrabutylammonium chloride or tetrabutylammonium bromide. The black-red polymer was dissolved in methanol and dedoped by adding a few drops of hydrazine. The final solution was evaporated. The resulting polymer was washed several times with a saturated solution of tetrabutylammonium chloride or tetrabutylammonium bromide in acetone, and by Soxlet extraction with acetone over a period of 6 hours, and then dried under reduced pressure to yield polymer 1 (0.32 g, 66%).

EXAMPLE 7

General Procedure for Optical Detection i) Synthetic Oligonucleotides

Figure 3:
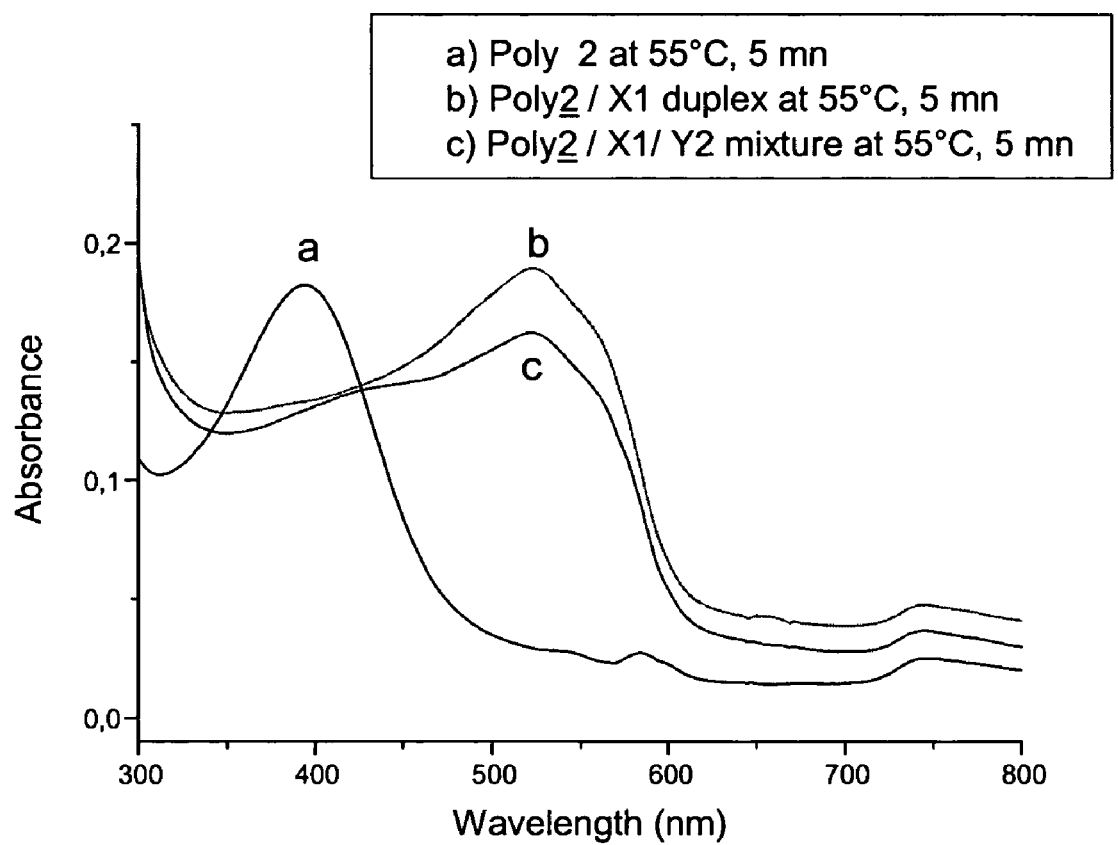
FIG. 3 shows the UV-visible absorption spectrum of a $2.4 \times 10^{-5}$ M (on a monomeric unit basis) solution of: a) polymer 2; b) polymer 2/X1duplex; c) polymer 2/X1/Y2 mixture, at 55° C. in 0.1M NaCl/H$_2$O.

In a quartz UV cuvette, 100 μL (7.47×10$^{-8}$ repeat units (RU) of positive charges) of a solution of polymer 2 were added to an aqueous solution (3 mL) containing either 0.1M NaCl or 10 Mm Tris buffer plus 0.1M NaCl (pH=8). The mixture was heated at 55° C. for 5 min and had a yellow appearance. 12 μL (7.47×10$^{-8}$ RU of negative charges) of oligonucleotide solution (capture probe) were then added and the resulting red solution kept at 55° C. for an additional 5 minutes. The appropriate oligonucleotide target was added to the solution at 55° C. over 5 minutes. A final yellow color is indicative of a positive result, meaning that perfect hybridization has taken place. On the other hand, a red or a red-pink color is representative of non specific or partial hybridization (two mismatches), respectively (FIGS. 1-3, respectively).

ii) PCR Products

Figure 4:
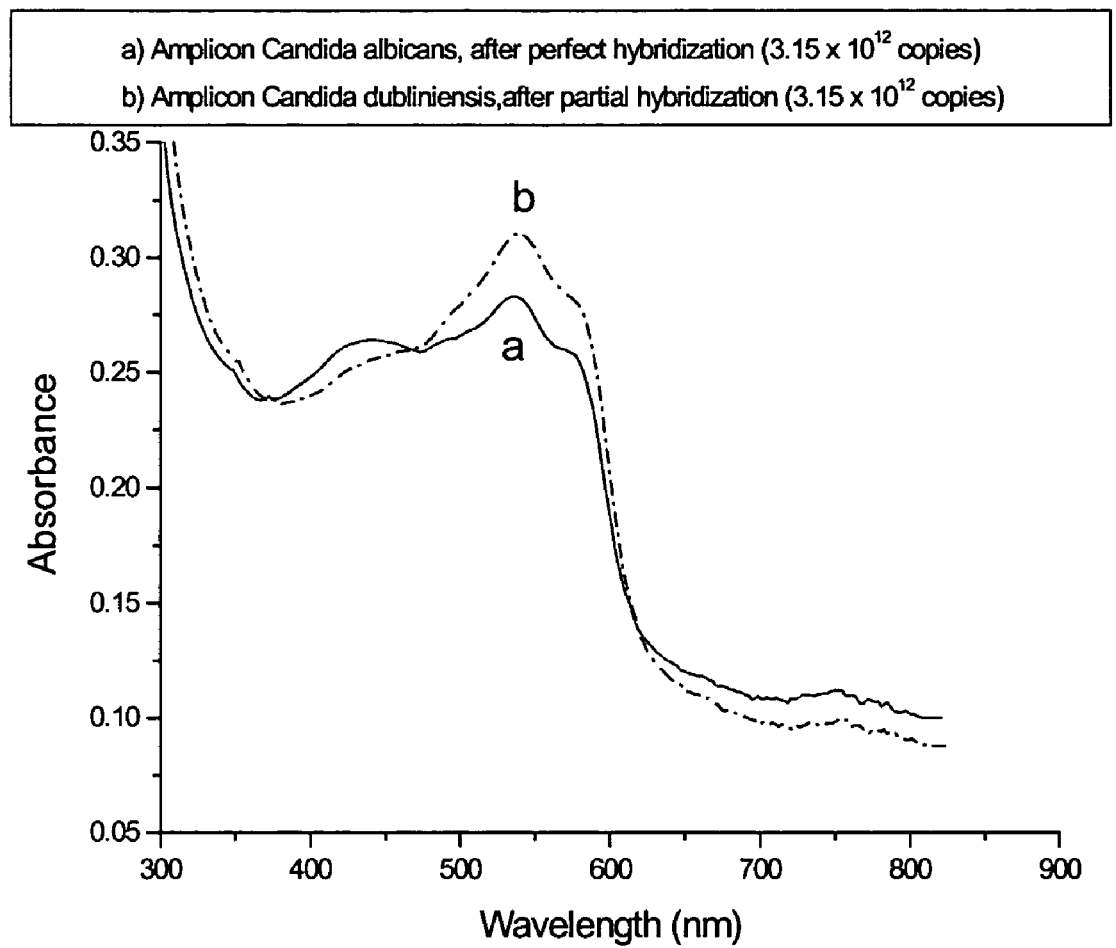
FIG. 4 shows the specific optical detection of *Candida albicans* versus *Candida dubliniensis* amplicons differing by only 2 nucleotides.

The amplicon (double stranded 149 base pairs) from the PCR product was pre-purified by <<QIAquick>> purchased from Qiagen. H$_2$O (90 μL) was added to a centrifuge tube followed by the addition of 6.7 μL (5.03×10$^{-9}$ mol of positive charge) of a solution of polymer 2, followed by the addition of the oligonucleotide capture probe Y1 (2 μL; 5.03 10$^{-9}$ mol of negative charge) and finally, by the addition of NaCl 1M (20 μL). The resulting mixture was heated at 50° C. for 10 min. The purified PCR product was freshly denatured, cooled in ice water and then added to the above solution. The hybridization reaction was kept at 50° C. for 35 min and the color change observed either visually or by UV measurement (FIG. 4).

EXAMPLE 8

General Procedure for Fluorescent Detection

A procedure identical to that described for optical detection was employed, with the exception of the use of a fluorospectrometer. The fluorescent intensity of a "duplex" (association between a positively charged polymer and an oligonucleotide capture probe) was weak or insignificant (practically zero) due to the fluorescent-quenching property of the aggregated form of the polymer. When perfect hybridization does occur, the fluorescent signal becomes more significant (FIG. 7).

EXAMPLE 9

General Procedure for Electrochemical Detection

The electrochemical test for hybridization was performed in conjunction with a control blank. 60 μL ($1.44 \times 10^{-8}$ mol of negative charge) of captured oligonucleotide Y1 were deposited on the aminated ITO electrode (S=50 mm$^2$) at ambient temperature for 5 min. After washing with water, 60 μL ($1.44 \times 10^{-9}$ mol of negative charge) of the target oligonucleotide X1 were added and the hybridization carried out at 55° C. over 20 minutes. The electrode was then cooled to room temperature over 10 min and washed twice with 0.3 M NaCl, 0.03 M NaOAc and 0.1% SDS (pH 7) and water. 100 μL ($1 \times 10^{-8}$ mol of positive charge) of a solution of polymer 1 or 2 was spread on the modified electrode for 5 min, followed by washing with $CH_3CN/H_2O$ (1/4) and water. Cyclic voltammograms were performed in aqueous 0.1 M NaCl solutions (FIGS. 10 and 11).

EXAMPLE 10

General Procedure for the Preparation of Electrodes Substituted With Covalent Probes i) Covalent Attachment of DNA Probes to an ITO Electrode (Polymer 2)

ITO slides are sonicated in hexanes (10 min), methanol (10 min) and ultrapure water (10 min), and are then treated with an aquaregia solution ($H_2O_2/H_2O/NH_4OH$, 1/5/1) at 40° C. over a 30 minute period. The resulting slides are rapidly washed with water, followed by sonication in water and in acetone, then dried with air, nitrogen or argon, and heated to 110° C. for 2 to 10 min. Following this, the slides are submerged for three hours, while under an inert atmosphere, in an acidified ethanol solution (1 mM acetic acid in 95% ethanol) containing 5% mercaptopropyltrimethoxysilane, followed by sonication in fresh ethanol (95%) and in ultrapure sterile water. Finally, the slides are heated at 110° C. for at least one hour, and cooled to room temperature before modification with DNA.

The washes, following DNA deposition, hybridization and polymer deposition, are carried out using an orbital shaker, unless otherwise stated. DNA attachment is carried out using a solution of SH-carbon$_{24}$-DNA in sodium citrate buffer (30 mM, pH=4, 50 μL) which is deposited onto each ITO slide, each spot forming a circle of about 1 cm in diameter. The deposition reaction is performed in a humidified chamber over a period of 20–24 hours. Any non-deposited DNA is drained off, and the slides washed with 5×SSC+0.1% Tween 20, followed by washings with 1×SSC+0.1% Tween 20 and NaCl 0.1M.

ii) Hybridization (ITO, Polymer 2)

50 μL of RC-DNA (Y1) or of probe X1 (blank test) (25 μM in 2×SSC), are deposited onto the DNA spot. The slides are then heated to 55° C. for about 3 hours while in a humid atmosphere, and then cooled to room temperature for 15 minutes. Any non-reacted DNA is drained off and the slides washed with 2×SSC, NaCl (0.1M), with 1×SSC+0.1% Tween 20 and with NaCl (0.1M).

iii) Polymer Deposition (ITO, Polymer 2)

Polymer 2 is deposited onto the electrodes. The slides are dipped vertically over a period of 5 minutes in a solution of polymer 2 (2 mL of $10^{-4}$ M in 0.01M NaCl) at room temperature. The slides are then dipped in 2 mL of a NaCl solution (0.01 M), followed by dipping in 2 mL of a $CH_3CN/H_2O$ (1/4) solution and finally, by dipping in 2 mL of a NaCl solution (0.01M).

iv) Hybridization (ITO, Polymer 3)

30 μL of Y1 (2.5 μM/NaCl 0.1M) are inserted into hybridization chambers which are placed onto the surface of the ITO electrode. The slides are heated for about two hours at 55° C. while in a humid atmosphere, and then cooled to room temperature. The hybridization chambers are removed and the slides washed with a 0.1M NaCl solution and finally dried with argon.

v) Polymer Deposition (ITO, Polymer 3)

Polymer 3 is deposited onto the electrodes. A 30 μL aqueous solution of polymer 3 ($10^{-4}$M) is inserted into hybridization chambers which are then placed onto the surface of the ITO electrode. The slides are heated at 55° C. for 20 minutes. The hybridization chambers are removed and the slides washed with a first portion of a 0.8M NaCl solution at 55° C., then washed with a new portion while cooling to room temperature. The slides are finally rinsed at room temperature with a 0.1M NaCl solution.

vi) Covalent Attachment of DNA Probes to a Gold Electrode (Polymer 2)

Gold slides are rinsed sequentially with hexanes, methanol and water. The plates are then treated with a pyranah solution ($H_2O_2$ 30%/$H_2SO_4$ concentrated; 30/70) over a period of about 15 minutes. The slides are then thoroughly washed with nanopure sterile water, and dried with argon.

DNA deposition is performed under inert atmosphere using 50 μL of a solution of SH-carbon$_{24}$-DNA (25 μM in 1M phosphate buffer (pH=7); $K_2HPO_4+KH_2PO_4$). The solution is deposited onto a 1 cm$^2$ surface, and treated for about 16 hours under inert atmosphere. Any non-reacted DNA is then drained off, and the slides sequentially washed with $H_2O$, 2×SSC, and sterile water.

Polymer 2 is deposited onto the electrodes. A 50 μL solution of polymer 2 ($10^{-5}$ M in 0.1M NaCl) is deposited onto the DNA spot and the slides heated to 55° C. for about 30 minutes. The slides are then washed repeatedly with a NaCl solution (0.1M) at room temperature.

Note that the order of additions does not have to follow that described in the above example, that is, a complementary (or a non-complementary or with mismatches) DNA strand is added to a covalently linked DNA strand, followed by the addition of a polymer solution. The polymer solution may be added prior to the addition of the complementary (or a non-complementary or with mismatches) DNA strand.

EXAMPLE 11

The Use of the Polymers of the Present Invention to Purify Nucleic Acids and Other Such Negatively Charged Molecules The polymers described in the present invention have high affinity for negatively charged molecules, especially nucleic acids. In addition, they are soluble in aqueous solution and very stable under a wide range of temperatures. Therefore, it is possible to use these properties to purify nucleic acids and other negatively charged molecules. Chromatographic separation would involve the following steps: (1) immobilizing the polymers; (2) applying the analyte to be separated onto the immobilized polymers under conditions such that electrostatic interactions are possible between the analyte and the polymer; and (3) eluting the analyte by applying conditions where electrostatic interactions between the analyte and the polymer are not favored.

Immobilization of the polymer can be achieved by covalently coupling the polymer to a suitable solid support such as glass beads, or to beads made of other types of polymers. Alternatively, coupling to a solid support could be achieved via electrostatic interactions, such as that demonstrated in Example 10. In the latter case, where a capture oligonucleotide is covalently attached to a solid support, the polymer would be expected to be eluted along with the analyte in the final elution step since it is attached only by electrostatic bonds. Color changes could even be used to monitor the chromatographic process.

Conditions for binding the analyte to the polymer would preferably involve solutions of low ionic charge, such as water, 0.1 M NaCl and 10 mM Tris buffer/0.1 M NaCl. Different washing conditions can be applied to remove any unwanted fractions of the analyte. pH changes could alternatively be used to obtain conditions for binding the analyte to the polymer.

Conditions for eluting the analyte involves solutions of high ionic charge, such as 1.0 M NaCl solution or any other solution comprising a sufficiently high counter ion concentration capable of competing for the electrostatic interactions with the polymer. Again, pH changes could alternatively be used to obtain conditions for eluting the analyte.

EXAMPLE 12

Detection of Messenger RNA

Purified, in vitro transcribed, polyadenylated messenger RNA of *Arabidopsis thaliana* gene coding for NAC1, was purchased from Stratagene. Perfectly matched complementary DNA oligonucleotide N1 (5' CGAGGCTTCCAT-CAATCTTA 3') was synthesized by phosphoramidite chemistry on a Perkin-Elmer 391 synthesizer. Unrelated Y2 DNA oligonucleotide was obtained in the same manner. All reagents and liquid handling material coming into contact with the RNA were either certified RNAse-free or treated with diethylpyrocarbonate (J. Sambrook and D. W. Russel, Molecular Cloning, A Laboratory Manual, CSHL Press, 2001) to inactivate RNAses. Fluorescence measurements were performed at 42.5° C. on a Variant Cary Eclipse spectrofluorometer with excitation set at 420±10 nm and fluorescence emission measured at 53015 nm, applying 1000 volts to the detector.

A duplex between polymer 2 and oligo N1 was formed by contacting $8.66 \times 10^{13}$ copies of oligo N1 with the equivalent amount of positive charges of polymer 2. The reaction was carried out at room temperature for thirty seconds in 2 μL of water. One μl of the duplex mixture was diluted in 2 mL of water and put into a quartz cuvette for measurement of the initial fluorescence signal. Thereafter, a triplex was formed at 42.5° C. by adding and mixing $8.66 \times 10^{13}$ copies of heat treated (2 minutes at 95° C.) NAC1 messenger RNA. Fluorescence of the triplex was measured. A similar duplex and triplex was also made using the DNA oligonucleotide Y2, which has no significant homology with the sequence of the NAC1 messenger RNA.

The fluorescence was significantly higher for the N1/polymer 2/NAC1 triplex than for the Y2/polymer 2/NAC1 triplex, thereby showing the ability of polymer 2 to distinguish between specific and nonspecific hybridization of 20 mers DNA oligonucleotides with messenger RNA.

In conclusion, a novel methodology has been developed that allows the detection of nucleic acids by simple optical and electrochemical means. This rapid, selective, and versatile method does not require any chemical reaction on the probes or the analytes, and is based on different electrostatic interactions and conformational structural changes between cationic poly(3-alkoxy-4-methylthiophene) derivatives and single-stranded oligonucleotides or double-stranded (hybridized) nucleic acid fragments. The present polymer-based technology is simple and specific and provides a flexible platform for the rapid detection of nucleic acids.

The polythiophenes are thermostable and autoclavable, hence allowing for a wide range of applications.

The terms and descriptions used herein are preferred embodiments set forth by way of illustration only, and are not intended as limitations on the many variations which those of skill in the art will recognize to be possible in practicing the present invention, as defined in the following claims.

REFERENCES

1) Fodor, S. P. A et al. *Science* 251, 767, (1991).
2) Livache, T. et al. *Nucleic Acids Res.* 22, 2912 (1994).
3) Tyagi, S.; Kramer, F. R. *Nature Biotechnology* 14, 303 (1996).
4) Mikkelson, S. R. *Electroanalysis* 8, 15 (1996).
5) Taton, T. A.; Mirkin, C. A.; Letsinger, R. L. *Science* 289, 1757, (2000).
6) Leclerc, M. *Adv. Mater.* 11, 1491, (1999).
7) McQuade, D. T.; Pullen, A. E.; Swager, T. M. *Chem. Rev.* 100, 2537 (2000).
8) Youssoufi, H. K.; Garnier, F.; Srivastava, P.; Godillot, P.; Yassar, A. *J. Am. Chem. Soc.*, 119,7388, (1997).
9) Bauerle, P.; Emge, A. *Adv. Matter.* 10, 324, (1998).
10) Garnier, F.; Youssoufi, H. K.; Srivastava, P.; Mandrand, B.; Delair, T. *Synth. Metals,* 100, 89, (1999).
11) ElKassmi, A.; Heraud, G.; Büchner, W.; Fache, F.; Lemaire, M. *J. Mol. Catal.,* 72, 299, (1992).
12) Balanda, P. B.; Ramey, M. B.; Reynolds, J. R. *Macromolecules,* 32, 3970, (1999).
13) Faïd, K.; Leclerc, M. *J. Chem. Soc., Chem. Commun.,* 2761, (1996).
14) Lucas, P.; Mehdi, N. E.; Ho, H. A.; Belanger, D.; Breau, L. *Synthesis,* 9, 1253, (2000).
15) Bonhôte, P.; Dias, A. P.; Papageorgiou, N.; Kalyanasundaram, K.; Grätzel, M. *Inorg. Chem.,* 35, 1168, (1996).
16) Chayer, M.; Faïd, K.; Leclerc, M. *Chem. Mater.,* 9, 2902, (1997).

17) Bronich, T. K.; Nguyen, H. K.; Eisenberg, A.; Kabanov, A. V. *J. Am. Chem. Soc.* 122, 8339, (2000).
18) Zammatteo, N; Jeanmart, L.; Hamels, S.; Courtois, S.; Louette, P.; Hevesi, L.; Remacle, J., *Anal. Biochem.*, 280, 143, (2000).
19) Chrisey, L. A.; Lee, G. U.; O'Ferrall, C. E. *Nucleic Acids Res.* 24, 3031, (1996).
20) Zammatteo, N.; Jeanmart, L.; Hamels, S.; Courtois, S.; Louette, P.; Hevesi, L.; Remacle, J. *J. Anal. Biochem.* 280,143, (2000).
21) Asanov, A. N.; Sarkisov, I. Y.; Oldham, P. B. Part of the *SPIE Conference on Clinical Diagnostics Systems and Technologies,* 3603,170, (1999).
22) Flink, S.; Frank, C. J. M.; Veggel, D. N. *Reinhoudt in Sensors Update,* Ed. H. Baltes, W. Gopel, J. Hesse, vol. 8, Chap.1 (2001).
23) Chen, L., McBranch, D. W., Wang, H. L., Hegelson, R., Wudl, F. & Whitten, D. G. Highly sensitive biological and chemical sensors based on reversible fluorescence quenching in a conjugated polymer. *PNAS* 96, 12287 (1999).
24) Ewbank, P. C., Nuding, G., Suenaga, H., McCullough, R. D., Shinkai, S. Amine functionalized polythiophenes: synthesis and formation of chiral, ordered structures on DNA substrates. *Tetrahedron Lett.* 42, 155 (2001).
25) Lvov, Y., Decher, G. & Sukhorukov, G. Assembly of thin layers by means of successive deposition of alternate layers of DNA and poly(allylamine). *Macromolecules* 26, 5396 (1993).
26) Lvov, Y. M., Lu, Z., Schenkman, J. B., Zu, X. & Rusling, J. F. Direct electrochemistry of myoglobin and cytochrome P450 in alternate layer-by-layer films with DNA and other polyions. *J. Am. Chem. Soc.* 120, 4073 (1998).
27) Faïd, K. & Leclerc, M. Responsive supramolecular polythiophene assemblies *J. Am. Chem. Soc.* 120, 5274 (1998)
28) Lenigk, R., Caries, M., Ip, N. Y., Sucher, N. J., *Langmuir,* 17, 2497 (2001).
29) Rogers, Y. H., Jiang-Baucon, P., Huang, Z. J., Bogdanov, V., Anderson, S., Boyce-Jacino, M. T., *Anal. Biochem.,* 266, 23 (1999).
30) Kumar, A., Larsson, O., Parodi, D., Liang, Z., *Nucl. Ac. Res.,* 28, e71 (2000).
31) Peterson, A. W., Heaton, R. J., Georgiadis, R. M., *Nucl. Ac. Res.,* 29, 5163 (2001).
32) Steel, A. B.; Levicky, R. L., Herne, T. M., Tarlov, M. J., *Biophys. J.,* 79, 975 (2000).
33) Peterlinz, K. A., Georgiadis, R. M., Herne, T. M., Tarlov, M. J., *J. Am. Chem. Soc.,* 119, 3401 (1997).

The invention claimed is:

1. A method for detecting the presence of a negatively charged polymer, comprising:
   a) contacting a target complementary to said negatively charged polymer with a cationic polymer to form a duplex, wherein the cationic polymer comprises the following formula:

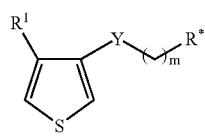

wherein:
   m is an integer ranging from 2 to 3;
   n is an integer ranging from 3 to 100;
   R* is a quartenary ammonium;
   Y is an oxygen atom or a methylene; and
   $R^1$ is a methyl group or a hydrogen atom;
   b) contacting said duplex with said negatively charged polymer; and
   c) detecting a change in electronic charge, fluorescence or color as an indication of the presence of said negatively charged polymer.

2. The method as defined in claim 1, wherein said negatively charged polymer is selected from the group consisting of: an acidic protein, a glycosaminoglycan, a hyaluronan, heparin, a chromatographic substrate, a culture substrate and a nucleic acid.

3. The method as defined in claim 2, wherein said negatively charged polymer is a nucleic acid.

4. The method as defined in claim 3, wherein said nucleic acid is DNA.

5. The method as defined in claim 3, wherein said nucleic acid is RNA.

6. The method as defined in claim 3, wherein said complementary target is a nucleic acid complementary to said negatively charged polymer.

7. The method as defined in claim 6, wherein said complementary target is a nucleic acid probe and said negatively charged polymer is a denatured PCR amplicon.

8. The method of claim 1, wherein said cationic polymer is ionically linked to said target complementary to said negatively charged polymer.

9. The method of claim 1, wherein said target complementary to said negatively charged polymer is linked to a solid support.

10. The method of claim 9, further comprising reacting said positively charged polymer with said target complementary to said negatively charged polymer, resulting in capture of said target complementary to said negatively charged polymer by said solid support forming a complex, and reacting said negatively charged polymer with said complex.

11. The method of claim 9, wherein said solid support is selected from the group consisting of an electrode, an optical fiber, a glass slide and glass beads.

12. The method of claim 9, further comprising purifying said negatively charged polymers.

13. The method of claim 12, wherein said negatively charged polymers are nucleic acids.

14. The method of claim 9, further comprising reacting said negatively charged polymer with said target complementary to said negatively charged polymer to form a complex between said negatively charged polymer and target complementary to said negatively charged polymer, wherein said positively charged polymer is reacted with said complex.

15. The method of claim 1, wherein:
   m is 3;
   R* is $^+Net_3$;
   Y is an oxygen atom; and
   $R^1$ is a methyl group.

16. The method of claim 1, wherein:
m is 2;
R* is
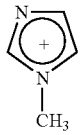
Y is an oxygen atom; and
$R^1$ is a methyl group.
17. The method of claim 1, wherein
m is 2;
R* is
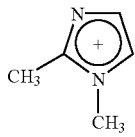
Y is an oxygen atom; and
$R^1$ is a methyl group.
18. The method of claim 1, wherein
m is 2;
R* is
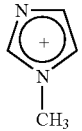
Y is a methylene group; and
$R^1$ is a hydrogen atom.
19. The method of claim 1, wherein the polymer formula is selected from the group consisting of:
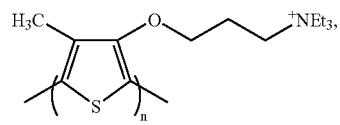
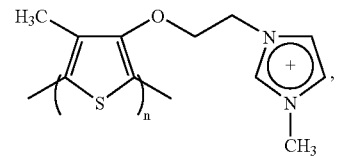
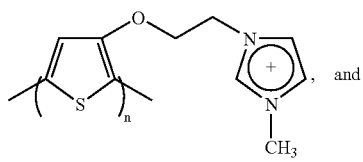, and
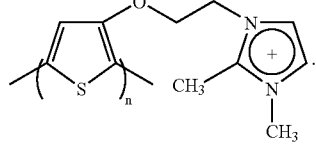
* * * * *